(12) United States Patent
Turker et al.

(10) Patent No.: US 9,034,645 B2
(45) Date of Patent: May 19, 2015

(54) METHODS OF IDENTIFYING INHIBITORS OF GENE SILENCING IN MAMMALIAN CELLS

(75) Inventors: Mitchell Turker, Portland, OR (US); Jon A. Oyer, Chicago, IL (US)

(73) Assignee: Oregon Health & Science University, Portland, OR (US)

( * ) Notice: Subject to any disclaimer, the term of this patent is extended or adjusted under 35 U.S.C. 154(b) by 422 days.

(21) Appl. No.: 12/992,168

(22) PCT Filed: May 27, 2009

(86) PCT No.: PCT/US2009/045333
§ 371 (c)(1),
(2), (4) Date: Nov. 11, 2010

(87) PCT Pub. No.: WO2009/154999
PCT Pub. Date: Dec. 23, 2009

(65) Prior Publication Data
US 2011/0088102 A1    Apr. 14, 2011

Related U.S. Application Data

(60) Provisional application No. 61/056,806, filed on May 28, 2008.

(51) Int. Cl.
C12N 5/00       (2006.01)
G01N 33/50      (2006.01)
C12N 15/85      (2006.01)

(52) U.S. Cl.
CPC ...... *G01N 33/5008* (2013.01); *A01K 2217/203* (2013.01); *A01K 2227/105* (2013.01); *A01K 2267/0393* (2013.01); *C12N 15/8509* (2013.01); *C12N 2830/006* (2013.01)

(58) Field of Classification Search
None
See application file for complete search history.

(56) References Cited

U.S. PATENT DOCUMENTS 6,858,773 B2    2/2005  Zhang et al.
7,291,461 B2    11/2007 Welch et al.

OTHER PUBLICATIONS

Bockamp et al (J Gene Med, 9(4): 308-18, 2007).*
Barreto et al., "Gadd45a promotes epigenetic gene activation by repair-mediated DNA demethylation," *Nature*, vol. 445, pp. 671-675, 2007.
Egger et al., "Inhibition of Histone Deacetylation Does Not Block Resilencing of p16 after 5-Aza-2'-Deoxycytidine Treatment," *Cancer Research*, vol. 67, pp. 346-353, 2007.
Karpf et al., "Reactivating the expression of methylation silenced genes in human cancer," *Oncogene*, vol. 21, pp. 5496-5503, 2002.
Kessler et al., "Effects of Nonsense Mutations on Nuclear and Cytoplasmic Adenine Phosphoribosyltransferase RNA," *Molecular and Cellular Biology*, vol. 16, No. 8, pp. 4426-4435, 1996.
Selker, "Trichostatin A causes selective loss of DNA methylation in Neurospora," *Proc. Natl. Acad. Sci. USA*, vol. 95, pp. 9430-9435, 1998.
Sutherland et al., "The histone deacetylase inhibitor trichostatin A reduces nickel-induced gene silencing in yeast and mammalian cells," *Mutation Research*, vol. 479, pp. 225-233, 2001.
Tchenio et al., "A Truncated form of the Human CAF-1 p150 Subunit Impairs the Maintenance of Transcriptional Gene Silencing in Mammalian Cells," *Molecular and Cellular Biology*, vol. 21, No. 6, pp. 1953-1961, 2001.
Turker, "Environmentally Induced Gene Silencing in Breast Cancer," *Oregon Health and Sciences University, Portland*, downloaded from the internet: http://www.dtic.mil/cgi-bin/GetTRDoc?Location=US &doc=GetTRDoc.pdf&AD=ADA473698, 2007 (8 pages).
Turker et al., "Region- and Cell type-Specific De Novo DNA Methylation in Cultured Mammalian Cells," *Somatic Cell and Molecular Genetics* vol. 17, No. 2, pp. 151-157, 1991.
Biacsi et al., "SIRT1 Inhibition Alleviates Gene Silencing in Fragile X Mental Retardation Syndrome," *PLoS Genetics*, vol. 4, No. 3, e1000017, 2008.
Chen et al., "Reactivation of silenced, virally transduced genes by inhibitors of histone deacetylase," *Proc. Natl. Acad. Sci. USA*, vol. 94, pp. 5798-5803, 1997.
Cheng et al., "Inhibition of DNA Methylation and Reactivation of Silenced Genes by Zebularine," *Journal of the National Cancer Institute*, vol. 95, No. 5, pp. 399-409, 2003.
Chou et al., "Transgenic Inhibitors of RNA Interference in Drosophila," *Fly (Austin)*, vol. 1, No. 6, pp. 311-316, 2007.
Foster et al., "A tetracycline-repressible transactivator approach suggests a shorter half-life for tyrosine hydroxylase mRNA," *Brain Research Protocols*, vol. 7, pp. 137-146, 2001.
Katz et al., "High-Frequency Epigenetic Repression and Silencing of Retroviruses Can Be Antagonized by Histone Deacetylase Inhibitors and Transcriptional Activators, but Uniform Reactivation in Cell Clones Is Restricted by Additional Mechanisms," *Journal of Virology*, vol. 81, No. 6, pp. 2592-2604, 2007.
Oyer et al., "Aberrant Epigenetic Silencing Is Triggered by a Transient Reduction in Gene Expression," *PLoS One*, vol. 4, e4832, 2009.
Yates et al., "Silencing of Mouse *Aprt* Is a Gradual Process in Differentiated Cells," *Mol. Cell. Biol.*, vol. 23, No. 13, pp. 4461-4470, 2003.
Zhu et al., "Silencing and Un-silencing of Tetracycline-Controlled Genes in Neurons," *PLoS One*, vol. 2, e533, 2007.

* cited by examiner

*Primary Examiner* — Deborah Crouch
*Assistant Examiner* — Magdalene Sgagias
(74) *Attorney, Agent, or Firm* — Klarquist Sparkman, LLP

(57) ABSTRACT

Disclosed herein are methods of identifying inhibitors of gene silencing or re-silencing, which can include repressing expression of a selectable marker gene in mammalian cells, treating the cells with at least one test compound, growing the cells under selective conditions, and quantifying the relative number of cells that live, wherein a change in the relative number of cells as compared to cells that were not treated with the test compound, identifies the compound as an inhibitor of gene silencing or re-silencing. Also disclosed herein are transgenic mice and isolated cell lines that are useful in the disclosed methods and kits for use in performing the disclosed methods.

19 Claims, 11 Drawing Sheets

SEQUENCE LISTING

<160> NUMBER OF SEQ ID NOS: 14

<210> SEQ ID NO 1
<211> LENGTH: 25
<212> TYPE: DNA

-continued

```
<213> ORGANISM: Artificial sequence
<220> FEATURE:
<223> OTHER INFORMATION: Synthetic oligonucleotide primer - Aprt
      promoter H2 region sense

<400> SEQUENCE: 1
gaggagggta tattttgttg taatg                                              25

<210> SEQ ID NO 2
<211> LENGTH: 29
<212> TYPE: DNA
<213> ORGANISM: Artificial sequence
<220> FEATURE:
<223> OTHER INFORMATION: Synthetic oligonucleotide primer - Aprt
      promoter H2 region antisense

<400> SEQUENCE: 2
aaaaacaaaa aaaaaataaa tatcaacac                                          29

<210> SEQ ID NO 3
<211> LENGTH: 23
<212> TYPE: DNA
<213> ORGANISM: Artificial sequence
<220> FEATURE:
<223> OTHER INFORMATION: Synthetic oligonucleotide primer - Aprt
      promoter H2 region nested sense

<400> SEQUENCE: 3
agtgtttgtg gttttagaga agg                                                23

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide primer - Aprt exon
      2-3 sense

<400> SEQUENCE: 4
ctcttggcca gtcacctgaa g                                                  21

<210> SEQ ID NO 5
<211> LENGTH: 25
<212> TYPE: DNA
<213> ORGANISM: Artificial sequence
<220> FEATURE:
<223> OTHER INFORMATION: Synthetic oligonucleotide primer - Aprt exon
      2-3 antisense

<400> SEQUENCE: 5
tctagacctg cgatgtagtc gatct                                              25

<210> SEQ ID NO 6
<211> LENGTH: 13
<212> TYPE: DNA
<213> ORGANISM: Artificial sequence
<220> FEATURE:
<223> OTHER INFORMATION: Synthetic oligonucleotide primer - Aprt exon
      2-3 TaqMan probe

<400> SEQUENCE: 6
cacgcacagc ggc                                                           13

<210> SEQ ID NO 7
<211> LENGTH: 24
<212> TYPE: DNA
<213> ORGANISM: Artificial sequence
```

```
<220> FEATURE:
<223> OTHER INFORMATION: Synthetic oligonucleotide primer - Aprt
      promoter sense

<400> SEQUENCE: 7
aacgtatgtc gaggtaggcg tgta                                              24

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide primer - Aprt
      promoter antisense

<400> SEQUENCE: 8
atctccttca tcacatctcg ag                                                22

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide primer - Aprt
      promoter TaqMan probe

<400> SEQUENCE: 9
tacctcctcc ctgcctccta ca                                                22

<210> SEQ ID NO 10
<211> LENGTH: 24
<212> TYPE: DNA
<213> ORGANISM: Artificial sequence
<220> FEATURE:
<223> OTHER INFORMATION: Synthetic oligonucleotide primer - Gapdh
      promoter sense

<400> SEQUENCE: 10
ttgagctagg actggataag cagg                                              24

<210> SEQ ID NO 11
<211> LENGTH: 24
<212> TYPE: DNA
<213> ORGANISM: Artificial sequence
<220> FEATURE:
<223> OTHER INFORMATION: Synthetic oligonucleotide primer - Gapdh
      promoter antisense

<400> SEQUENCE: 11
aagaagatgc ggccgtctct ggaa                                              24

<210> SEQ ID NO 12
<211> LENGTH: 26
<212> TYPE: DNA
<213> ORGANISM: Artificial sequence
<220> FEATURE:
<223> OTHER INFORMATION: Synthetic oligonucleotide primer - Gapdh
      promoter TaqMan probe

<400> SEQUENCE: 12
tataaatacg gactgcagcc ctccct                                            26

<210> SEQ ID NO 13
<211> LENGTH: 21
<212> TYPE: DNA
<213> ORGANISM: Artificial sequence
<220> FEATURE:
```

-continued

```
<223> OTHER INFORMATION: Synthetic oligonucleotide primer - Mage-a
      promoter sense

<400> SEQUENCE: 13
gttctagtgt ccatattggt g                                           21

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide primer - Mage-a
      promoter antisense

<400> SEQUENCE: 14
aactggcaca gcatggagac                                             20
```

METHODS OF IDENTIFYING INHIBITORS OF GENE SILENCING IN MAMMALIAN CELLS

CROSS REFERENCE TO RELATED APPLICATIONS

This is the §371 U.S. National Stage of International Application No. PCT/US2009/045333, filed May 27, 2009, which was published in English under PCT Article 21(2), which in turn claims the benefit of U.S. Provisional Application No. 61/056,806, filed May 28, 2008, which is incorporated herein in its entirety.

ACKNOWLEDGMENT OF GOVERNMENT SUPPORT

This invention was made with United States government support under grant 5R21ES015191 from the National Institutes of Health, and grant DOD BC052492 from the Department of Defense; the United States government has certain rights in the invention.

FIELD

This disclosure relates to methods of identifying inhibitors of gene silencing and re-silencing, as well as mammalian cell lines and transgenic mice used in such methods.

BACKGROUND

The conversion of a normal diploid cell to one that is malignant is a prolonged process. This conversion takes months to years in rodents and humans, respectively, and it involves widespread changes in gene expression (Bartek and Lucas, *Nature* 411:1001-1002, 2001; Nebert, *Toxicol.* 181-182:131-141, 2002). Separation of causal changes in gene expression from those that are a consequence of the malignant process is sometimes difficult; yet a causal role for tumor suppressor gene inactivation in initiating and maintaining the malignant phenotype is clear (Weinberg, *Ann. NY Acad. Sci.* 758:331-338, 1995). Tumor suppressor genes have a variety of functions including the control of cellular growth and the recognition and repair of DNA damage (Baylin et al., *Hum. Mol. Genet.* 10:687-692, 2001; Oliveira et al., *Am. J. Clin. Pathol.* 124:S16-28, 2005). One pathway for tumor suppressor gene inactivation is mutation (Turker, *Semin. Cancer Biol.* 8:407-419, 1998; Turker, *Mutagenesis* 18:1-6, 2003) and a second pathway is gene silencing (Fruhwald and Plass, *Mol. Genet. Metab.* 75:1-16, 2002; Jones and Laird, *Nat. Genet.* 21:163-167, 1999; Baylin et al., *Adv. Cancer Res.,* 72:141-196, 1998; Laird, *Hum. Mol. Genet.* 14:R65-76, 2005). While a routine DNA sequence analysis will not reveal changes in the promoter or coding region of a silenced allele, relative to its expressed counterpart, a bisulfite sequence analysis usually reveals increased levels of promoter region DNA methylation (Chen et al., *Nat. Genet.* 33:197-202, 2003; Toyooka et al., *Cancer Res.* 62:3384-3386, 2002; Lee et al., *Cancer Res.* 61:6688-6692, 2001; Worm et al., *Oncogene* 19:5111-5115, 2000; Pogribny and James, *Cancer Lett.* 187:69-75, 2002). Chromatin changes are associated with promoter region DNA methylation in part because methyl binding proteins recruit repressive factors such as histone deacetylases (Bird and Wolffe, *Cell* 99:451-545, 1999; Ng and Bird, *Curr. Opin. Genet. Dev.* 9:158-163, 1999). Thus, a marker for silencing in cancer is a hypermethylated promoter combined with repressive chromatin modifications (Palii and Robertson, *Crit. Rev. Eukaryot. Gene Expr.* 17:295-316, 2007).

DNA methylation-associated silencing is a dominant pathway for gene inactivation in human cancers (Jones and Laird, *Nat. Genet.* 21:163-167, 1999). For example, silencing of critical genes such as MLH1 (Murata et al., *Oncogene* 21:5696-5703, 2002), BRCA1 (Esteller et al., *J. Natl. Cancer Inst.* 92:564-569, 2000; Matros et al., *Breast Cancer Res. Treat.* 91:179-186, 2005), E-CAD (E-cadherin) (Graff et al., *Cancer Res.* 55:5195-5199, 1995; Lombaerts et al., *Br. J. Cancer* 94:661-671, 2006), and ERα (estrogen receptor alpha) (Kim et al., *Int. J. Mol. Med.* 14:289-293, 2004; Yan et al., *J. Mammary Gland Biol. Neoplasia* 6:183-192, 2001) is more common than mutation in sporadic breast cancers. Based on observations such as these, one approach for treating cancer is to use pharmacological and/or dietary interventions to reactivate silenced tumor suppressor genes (Gronbaek et al., *Apmis* 115:1039-1059, 2007; Mund et al., *Epigenetics* 1:7-13, 2006). A potential flaw with this approach, however, is that chemically reactivated alleles retain epigenetic chromatin marks consistent with silenced states (Egger et al., *Cancer Res.* 67:346-353, 2007; McGarvey et al., *Cancer Res.* 66:3541-3549, 2006), which suggests that reactivated alleles frequently re-silence because they retain epigenetic "scars" of silencing. Therefore, identification of inhibitors of gene silencing, such as compounds that reduce or prevent epigenetic changes, is needed to identify potential chemopreventive agents.

SUMMARY

Disclosed herein are methods of identifying inhibitors of gene silencing or re-silencing in mammalian cells. Such identified inhibitors can then be further tested in vitro and in vivo for their ability to reduce or inhibit gene silencing. In some examples such inhibitors can be used to treat or prevent a neoplasm, such as cancer, for example in a human or other mammalian subject.

In particular examples, the disclosed methods include repressing expression of a selectable marker gene in mammalian cells, such as a human cell line. The cells having the repressed gene are then contacted or incubated with one or more test compounds, grown under selective conditions to identify cells in which gene silencing is inhibited, and the number of cells that survive or live quantified, wherein a change in the number of live cells as compared to the number of live cells that are not treated with the test compound identifies the compound as an inhibitor of gene silencing.

In additional examples, the disclosed methods include inducing gene silencing by repressing expression of a selectable marker gene in mammalian cells, such as a human cell line. Cells having the silenced gene which has undergone reactivation of the selectable marker are then selected, contacted or incubated with one or more test compounds, and grown under selective conditions to identify cells in which gene re-silencing is inhibited. The number of cells that survive or live are quantified, wherein a change in the number of live cells as compared to the number of live cells that are not treated with the test compound identifies the compound as an inhibitor of gene re-silencing. In some examples, reactivation of the selectable marker is spontaneous.

In some embodiments, the cells used in the disclosed methods are mammalian cells growing in cell culture. In additional embodiments, the cells used in the disclosed methods are part of a transgenic mouse, wherein the test compound is administered to the mouse, for example in the diet or drinking water, by dermal adsorption, by inhalation, or by injection.

Also disclosed herein are cell lines that may be used in the disclosed methods of identifying an inhibitor of gene silencing or re-silencing. In some examples, the cell line includes a repressible promoter operably linked to a selectable marker. In a particular example, the cell line is stably transfected with a tetracycline (tet)-responsive transcription activator protein operably linked to a constitutive promoter and a selectable marker operably linked to a tet-repressible promoter.

Disclosed herein are transgenic mice that may be used in the disclosed methods of identifying an inhibitor of gene silencing or re-silencing. In some examples the transgenic mouse includes a repressible promoter operably linked to a selectable marker, such as mouse Aprt. In some examples the transgenic mouse further includes a transcription activator protein operably linked to a constitutively active promoter.

Also disclosed herein are kits for identifying compounds that are inhibitors of gene silencing or re-silencing. In some examples, the kits include one or more cell lines including a repressible promoter operably linked to a selectable marker.

The foregoing and other features will become more apparent from the following detailed description, which proceeds with reference to the accompanying figures.

BRIEF DESCRIPTION OF THE DRAWINGS

FIG. 1 is a schematic drawing of the tet-off system.

FIG. 13 is a series of bar graphs showing histone H3 modifications determined by chromatin immunoprecipitation in parental cells with active Aprt expression (H22) and Dap-resistant cell lines with silenced Aprt expression (D7, D3, and D3S1).

FIG. 14 is a series of bar graphs showing Aprt re-silencing frequency.

SEQUENCE LISTING

Figure 1A:
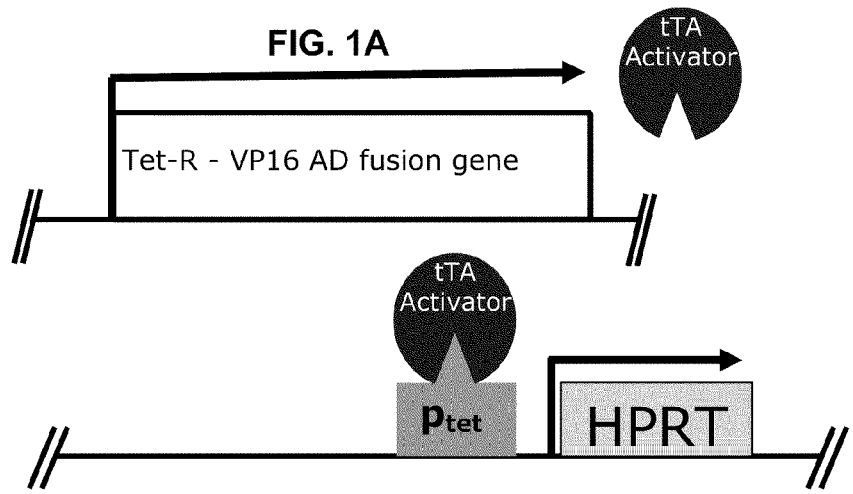
FIG. 1A shows that expression of the human HPRT cDNA is under the control of an activator protein containing a DNA binding domain and a VP-16 activation domain (tTA). The HPRT containing construct is termed $P_{tet}$-HPRT. Binding of the activating protein to the tet binding sites ($P_{tet}$) leads to HPRT expression due to the presence of the herpes simplex virus VP-16 activation domain at the promoter.

Any nucleic acid and amino acid sequences listed herein or in the accompanying sequence listing are shown using standard letter abbreviations for nucleotide bases, and three letter code for amino acids, as defined in 37 C.F.R. 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Nov. 9, 2010, and is 3,629 bytes, which is incorporated by reference herein.

SEQ ID NOs: 1 and 2 show sense and antisense Aprt promoter H2 region primers, respectively.

SEQ ID NO: 3 shows a nested sense Aprt promoter H2 region primer.

SEQ ID NOs: 4 and 5 show sense and antisense Aprt exon 2-3 splice site primers, respectively.

SEQ ID NO: 6 shows a Aprt exon 2-3 TaqMan probe.

SEQ ID NOs: 7 and 8 show sense and antisense Aprt promoter primers, respectively.

SEQ ID NO: 9 shows a Aprt promoter TaqMan probe.

SEQ ID NOs: 10 and 11 show sense and antisense Gapdh promoter primers, respectively.

SEQ ID NO: 12 shows Gadph promoter TaqMan probe.

SEQ ID NOs: 13 and 14 show sense and antisense Mage-a promoter primers, respectively.

DETAILED DESCRIPTION

I. Abbreviations

APRT: adenine phosphoribosyltransferase
AzA: azaserine and adenine
5-Aza-dC (or AzaC): 5-aza-deoxycytidine
ChIP: chromatin immunoprecipitation
DAP: 2,6-diaminopurine
Dox: doxycycline
ES: embryonic stem
GPT: xanthine-guanine phosphoribosyltransferase
HDAC: histone deacetylase
HPRT: hypoxanthine-guanine phosphoribosyltransferase
$P_{tet}$: tetracycline repressible promoter
Puro: puromycin
SFN: sulforaphane
Tet: tetracycline
TG: 6-thioguanaine
TK: thymidine kinase
TSA: trichostatin A II. Terms Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. All sequences identified by Genbank Accession No. are hereby incorporated by reference on May 28, 2008. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN1-56081-569-8).

In order to facilitate review of the various embodiments of the invention, the following explanations of specific terms are provided:

Administration: To provide or give a subject an agent, such as a test compound (such as a candidate inhibitor of gene silencing), alone or in combination with another agent, by any effective route. Exemplary routes of administration include, but are not limited to, oral (such as in the food or water), injection (such as subcutaneous, intramuscular, intradermal, intraperitoneal, and intravenous), or topical routes.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a selectable marker gene is expressed when it is transcribed into an RNA. In another example, a selectable marker gene is expressed when its RNA is translated into an amino acid sequence. The term "expression" is used herein to denote either transcription or translation.

Gene silencing: Conversion of an actively expressed gene, or construct, to a gene, or construct, whose expression is significantly reduced or even completely inhibited, which occurs without a change in the primary DNA sequence. Transcriptional silencing refers to the significant reduction or inhibition of transcription of a gene, for example a coding nucleic acid sequence. Post-transcriptional silencing refers to silencing at the RNA level and which results in the inhibition of translation, for example by small inhibitory RNAs (siRNAs). Re-silencing includes gene silencing in which a silenced gene has been reactivated (for example, gene expression is restored), and then subsequently silenced again.

Histone deacetylase (HDAC): A family of proteins that catalyze deacetylation of histone lysine residues. HDACs are classified into three families based on structural homology and co-factor dependence. Class I and II HDACs require zinc as a cofactor, while Class III HDACs require nicotinamide adenine dinucleotide (NAD) for enzyme activity. In cancer, HDACs are recruited to the promoter regions of tumor suppressor genes and result in inappropriate transcriptional repression (such as gene silencing), contributing to tumorigenesis.

Inhibition of HDAC function can reverse transcriptional gene silencing and inhibitors of HDACs have been shown to have anti-tumor activity. HDAC inhibitors include diverse compounds, such as short-chain fatty acids (for example, sodium butyrate and valproic acid), epoxides (for example, depudecin and trapoxin), cyclic peptides (for example, apicidin and depsipeptide), hydroxamic acids (for example, trichostatin A, suberoylanilide hydroxamic acid (SAHA), oxamflatin, scriptaid, and pyroxamide), benzamides (for example, MS-275 and CI-994), and other hybrid compounds (for example, SK-7068).

Inhibitor: A compound that reduces or prevents a particular cellular event (for example, gene silencing). In one example, an inhibitor is a test compound that decreases gene silencing or re-silencing by a statistically significant amount, such as at least 10%, at least 20%, at least 50%, at least 95%, or even 100% as compared to gene silencing that occurs in the absence of the inhibitor. In some examples, the inhibitor may be a histone deacetylase inhibitor.

Isolated: An "isolated" biological component (such as a cell, nucleic acid molecule, protein, or organelle) has been substantially separated or purified away from other biological components in the cell or the organism in which the component naturally occurs, such as other cells, chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Oligonucleotide: An oligonucleotide is a plurality of nucleotides joined by native phosphodiester bonds, between about 4 and about 500 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Particular oligonucleotides and oligonucleotide analogs include linear sequences up to about 300 nucleotides in length, for example a sequence (such as DNA or RNA) that is at least 6 bases, for example at least 8, 10, 15, 20, 25, 30, 35, 40, 45, 50, 100 or even 200 or more bases long, or from about 6 to about 50 bases, for example about 10-25 bases, such as 12, 15, 20, or 25 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame. In some examples, a promoter sequence is operably linked to a protein encoding sequence, such that the promoter drives transcription of the linked nucleic acid and/or expression of the protein.

Promoter: Promoters are sequences of DNA near the 5' end of a gene that act as a binding site for RNA polymerase, and from which transcription is initiated. A promoter includes necessary nucleic acid sequences near the start site of transcription, such as, in the case of a polymerase II type promoter, a TATA element. In one embodiment, a promoter includes an enhancer. In another embodiment, a promoter includes a repressor element.

Promoters may be constitutively active, such as a promoter that is continuously active and is not subject to regulation by external signals or molecules. In some examples, a constitutive promoter is active such that expression of a sequence operably linked to the promoter is expressed ubiquitously (for example, in all cells of a tissue or in all cells of an organism and/or at all times in a single cell or organism, without regard to temporal or developmental stage). In a particular example, a constitutively active promoter is a cytomegalovirus promoter.

Promoters may be repressible, such that expression of a sequence operably linked to the promoter can be reduced to low or undetectable levels, or eliminated. A repressible promoter may be repressed by direct binding of a repressor molecule (such as binding of the trp repressor to the trp operator in the presence of tryptophan). In some examples, the promoter is activated by binding of a transcription activator protein and the promoter is repressible by addition of a compound that binds to the transcription activator and prevents its interaction with the repressible promoter. In a particular example, a repressible promoter is a tetracycline repressible promoter. In other examples, a repressible promoter is a promoter that is repressible by environmental conditions, such as hypoxia or exposure to metal ions.

Repress/repressible: To prevent or significantly reduce expression, for example, by preventing or blocking transcription of a gene. A gene or promoter is repressible if its expression or activity can be reduced or suppressed by preventing binding of a transcription activator. In one example, a repressible promoter is the tet-repressible promoter, wherein expression of a gene linked to the promoter can be prevented by binding of tetracycline or a tet analog to a tetracycline responsive transcription activator.

RNA (ribonucleic acid): RNA is a long chain polymer which includes nucleic acids joined by 3'-5' phosphodiester bonds. The repeating units in RNA polymers are four different nucleotides, each of which comprises one of the four bases, adenine, guanine, cytosine, and uracil bound to a ribose sugar to which a phosphate group is attached. In general, DNA is transcribed to RNA by an RNA polymerase. RNA transcribed from a particular gene contains both introns and exons of the corresponding gene; this RNA is also referred to as pre-mRNA. RNA splicing subsequently removes the intron sequences and generates a messenger RNA (mRNA) molecule, which can be translated into a polypeptide. Triplets of nucleotides (referred to as codons) in an mRNA molecule code for each amino acid in a polypeptide, or for a stop signal.

Except where single-strandedness is required by the text herein, RNA molecules, though written to depict only a single strand, encompass both strands of a double-stranded RNA molecule.

Antisense RNA is single-stranded RNA that is complementary to an mRNA strand transcribed within a cell. Antisense RNA may be introduced into a cell to inhibit translation of a complementary mRNA by hybridizing to it, leading either to degradation of the resulting double-stranded RNA by a ribonuclease (such as RnaseH), or by physically blocking the translation machinery (see e.g. Dias and Stein, *Mol. Cancer. Ther.* 1:347-355, 2002). RNA interference (RNAi) is the process of mRNA degradation that is induced by double-stranded RNA in a sequence-specific manner. In some examples, RNAi molecules include microRNAs (miRNAs), small interfering RNAs (siRNAs), and repeat-associated small interfering RNAs (rasiRNAs).

Selectable marker: A gene introduced into a cell, especially a bacterium or cells in culture, which confers a trait suitable for artificial selection. In some examples, expression of a selectable marker allows for positive selection. A positive selectable marker refers to a gene encoding a product that enables only the cells that express the gene to survive and/or grow under certain conditions (such as in the presence of a particular drug or analyte). Selectable markers that may be used for positive selection include antibiotic resistance genes (such as genes that confer resistance to neomycin, hygromycin, puromycin, blasticidin S, ampicillin, or kanamycin) and genes which confer resistance to killing by nucleoside analogs (such as cytidine deaminase).

In other examples, expression of a selectable marker allows for negative selection. A negative selectable marker refers to a gene encoding a product that can be used to selectively kill and/or inhibit growth of cells that express the selectable marker under certain conditions (such as in the presence of a drug or analyte). Selectable markers that may be used for negative selection include HPRT, APRT, thymidine kinase (TK), xanthine-guanine phosphoribosyltransferase (GPT), or adenine deaminase.

Selective conditions: Treatment with a compound or under conditions which allow detection of cells expressing or lacking expression of a particular gene (referred to as a selectable marker). In some examples, selective conditions are those conditions which decrease survival of cells which lack expression of a selectable marker gene. For example, the selective conditions may be growth of cells or treatment of an organism with an antibiotic (such as puromycin, hygromycin, G418, ampicillin, blasticidin S, or kanamycin), such that cells that do not express the appropriate antibiotic resistance gene (such as ampicillin resistance gene (β-lactamase), neomycin resistance gene (NptII), hygromycin resistance gene (Hph), kanamycin resistance gene (Kanr), puromycin resistance gene (Pac), or blasticidin S resistance gene (Bsr)) have reduced survival as compared with cells that do express the appropriate antibiotic resistance gene. In other examples, selective conditions include those conditions which decrease survival of cells which express a selectable marker gene. For example, the selective conditions may be growth of cells or treatment of an organism with a nucleoside analog (such as TG, DAP, or trifluorothymidine), such that cells that express the appropriate enzyme (such as HPRT, APRT, or TK, respectively) have reduced survival as compared with cells that do not express the appropriate enzyme. In additional examples, selective conditions are those conditions which allow detection of expression of a selectable marker. For example, the selective conditions may be growth of cells or treatment of an organism with conditions, such as an enzyme substrate or exposure to a particular wavelength of light, such that cells that express a particular selectable marker, such as luciferase or green fluorescent protein, respectively, are detected.

Subject: Living multi-cellular vertebrate organisms, a category that includes human and non-human mammals (such as laboratory or veterinary subjects).

Test compound: A candidate inhibitor of gene silencing that is used in the disclosed methods. A test compound can include any small organic molecule, or a biological entity, for example a protein (such as an antibody or a peptide), a sugar, a nucleic acid (such as an antisense oligonucleotide, a ribozyme, or RNAi molecule) or a lipid. The test compound may be isolated, or may be part of a mixture (for example two or more test compounds). The test compound or mixture of test compounds may also include additional components, such as diluents, solvents, pharmaceutically acceptable carriers, or other compounds. In a particular example, a test compound is a food or food component.

Tetracycline (tet): A broad-spectrum polyketide antibiotic produced by the *Streptomyces* bacterium, used to treat many bacterial infections. The basic structure of tet and its analogs includes four hydrocarbon rings. Tet and tet analogs inhibit protein synthesis by inhibiting the binding of aminoacyl-tRNA to the mRNA-ribosome complex. They do so mainly by binding to the 30S ribosomal subunit in the mRNA translation complex. There are a number of naturally-occurring tet analogs, including chlortetracycline, oxytetracycline, and demecocycline. Tet analogs also include semi-synthetic tetracyclines, such as doxycycline, lymecycline, meclocycline, methacycline, minocycline, rolitetracycline, and tigecycline. In one example, a tet analog is doxycycline.

Transcription activator: A protein that binds to DNA and stimulates transcription of nearby genes. Transcription activators have an activation domain and a DNA binding domain; some activators also have dimerization and ligand binding domains. In a particular example, a transcription activator is a chimeric protein comprising a tet-responsive factor (such as a DNA binding domain that binds to a tet-responsive promoter element) linked to an activation domain of a herpes simplex virus transcriptional activator VP-16.

Transduced or Transfected: A virus or vector transduces or transfects a cell when it transfers nucleic acid into the cell. A cell is "transfected" by a nucleic acid transduced into the cell when the DNA becomes stably replicated by the cell, either by incorporation of the nucleic acid into the cellular genome, or by episomal replication.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgenic Cell: Transformed cells which contain foreign, non-native DNA.

Transgenic mouse: A transformed mouse that contains foreign, non-native DNA. In one example, the non-native DNA includes an exogenous or native repressible promoter operably linked to the Aprt gene. In additional examples, the non-native DNA includes a tet-repressible promoter operably linked to an Hprt gene and a constitutive promoter operably linked to a tet activator protein.

III. Overview of Several Embodiments

Disclosed herein are methods of identifying agents that significantly reduce or inhibit gene silencing (such as reduce or prevent gene silencing or reduce or prevent re-silencing of a silenced and re-activated gene). In particular examples, the method includes repressing expression of a selectable marker gene in mammalian cells; contacting the cell that includes the repressed selectable marker with at least one test compound (such as 1, 2, 3, or 4 test compounds); growing said cells under selective conditions; and quantifying cells that survive, wherein a change (such as a statistically significant increase or decrease) in the relative number of live cells as compared to the relative number of cells that are not treated with the test compound identifies the compound as an inhibitor of gene silencing.

In some examples, the selectable marker gene includes a repressible promoter operably linked to a selectable marker. Cells which express the selectable marker under the control of a repressible promoter can be treated with a compound or under conditions that repress (such as reduce or inhibit) the expression of the selectable marker. Repression of selectable marker gene expression does not require 100% inhibition of expression; decreases of expression of at least 90%, at least 95%, at least 98%, or at least 99% may be sufficient. In at least some cells, repression of expression of the selectable marker induces gene silencing of the selectable marker.

In some examples the repressible promoter includes an exogenous repressible promoter, such as a tet-repressible promoter or a GAL4-repressible promoter. When the promoter is a tet-repressible promoter, expression of the selectable marker is repressed by addition of tet or a tet analog (for example doxycycline) in the cell culture medium, for example, about 1 nM to about 100 µM Dox for about 1 week to about 3 weeks. If the promoter is a GAL4-repressible promoter, the selectable marker is expressed when cells are grown in the presence of galactose and a GAL80 protein, and expression of the selectable marker is repressed by growth of the cells in the absence of galactose. In additional examples, the repressible promoter includes a mammalian repressible promoter, such as a BRCA1, MLH1, E-cadherin, estrogen receptor α, androgen receptor, Mcp1, Zac1, Gas1, or Serpin gene promoter. When the promoter is a mammalian repressible promoter, expression of the selectable marker is repressed by treating the cells with conditions that repress expression from the promoter (such as hypoxia or in the presence of metals). In some examples, the hypoxic conditions include growth of cells under atmospheric conditions containing about 95% nitrogen and about 5% oxygen for about 3 days to 3 weeks, such as about 5 days to 2 weeks, about 10 days to 18 days, or about 1 week. In other examples, cells are grown in the presence of a metal (such as iron sulfate, nickel chloride, or cobalt chloride), from about 10 µM to about 1 mM for about 1 day to about 3 weeks.

Following repression of expression of the selectable marker (and in some instances, gene silencing), the cells are contacted with one or more test compounds which are candidate inhibitors of gene silencing. In some examples, 1, 2, 3, 4, 5, 6, 7, 8, 9, or 10 compounds are contacted with the cell, for example simultaneously. The test compound is introduced in the cell culture medium for a suitable period of time, such as at least 1 hour, at least 2 hours, at least 6 hours, or even at least 24 hours, such as about 6 hours to about 3 weeks, for example, about 6 hours, 12 hours, 24 hours, 2 days, 3 days, 5 days, 1 week, 2 weeks, or 3 weeks. In some examples, the exposure to the test compound is for the same duration as the exposure to the treatment that represses selectable marker expression.

The amount of test compound applied to the cells is an amount that inhibits gene silencing, such as about 1 nM to about 1 mM, for example, about 1 nM to about 100 µM, about 10 nM to about 10 µM, or about 100 nM to about 1 µM. The amount of test compound that inhibits gene silencing may vary depending on the particular compound. Methods for determining an appropriate dose of a particular compound are known to those of skill in the art. For example, an appropriate dose may be determined by treating cells with a range of concentrations, and determining an $LD_{50}$ or $IC_{50}$ for the inhibition of gene silencing. In other examples, an appropriate dose may be determined by treating a subject (such as a transgenic mouse) with a range of concentrations to determine the maximum tolerated dose.

In particular examples, the cells are grown under conditions that repress expression of the selectable marker for a period of time prior to treatment with the test compound. For example, the cells may be grown under conditions that repress selectable marker gene expression for about 1 day to about three weeks (such as about 3 days, about 5 days, about one week, about two weeks or about three weeks) in order to repress expression or induce gene silencing. The test compound is then added to the cells for a period of time (such as about 6 hours to about one week, for example about one day), to inhibit gene silencing. In other examples, the conditions that repress expression of the selectable marker and administration of the test compound may be concurrent. In additional examples, the conditions that repress expression of the selectable marker may be immediately prior to, or overlap with, administration of the test compound. In one particular example, the conditions that repress expression of the selectable marker are applied to the cells for seven days. On the seventh day, the test compound is applied to the cells, simultaneously with the conditions that repress selectable marker expression.

In some examples, following repression of selectable marker expression and administration of at least one test compound, the cells are grown under selective conditions. In some examples, the selectable marker is a negative selection marker and the selective conditions are such that the cells die if the gene silencing of the selectable marker is inhibited by the test compound. The selective conditions are those which are appropriate for the negative selectable marker. For example, when the selectable marker is hypoxanthine-guanine phosphoribosyltransferase (HPRT), the cells are grown in the presence of a suitable concentration of 6-thioguanine (TG), for example about 1 µg/ml to about 20 µg/ml TG for about 1-3 weeks. Cells which express HPRT (such as when HPRT silencing is reduced or inhibited) will die in the presence of TG, while cells which do not express HPRT (such as when HPRT is silenced) will live in the presence of TG. Likewise, when the selectable marker is adenine phosphoribosyltransferase (APRT), the cells are grown in the presence of a suitable concentration of 2,6-diaminopurine (DAP), for example about 10 µg/ml to about 100 µg/ml DAP for about 1-3 weeks. Cells which express APRT (such as when APRT silencing is reduced or inhibited) will die in the presence of DAP, while cells which do not express APRT (such as when APRT is silenced) will live in the presence of DAP.

In other examples, the selectable marker is a positive selection marker and the selective conditions are such that the cells live if the gene silencing of the selectable marker is inhibited by the test compound. The selective conditions are those which are appropriate for the positive selectable marker. For example, when the selectable marker is an antibiotic resistance marker (such as hygromycin, neomycin, puromycin, blasticidin S, ampicillin, or kanamycin), the cells are grown in the presence of a suitable concentration of the appropriate antibiotic. Cells which express the antibiotic resistance gene (such as when gene silencing is reduced or inhibited) will live in the presence of the antibiotic, while cells which do not express the antibiotic resistance gene (such as when the gene is silenced) will die in the presence of the antibiotic.

In yet further examples, the selectable marker may be a reporter gene, such as luciferase or a green fluorescent protein. The selective conditions are those conditions that allow detection of expression of the reporter protein, such as presence of an appropriate substrate or exposure to an appropriate wavelength of light. Cells which express the reporter gene will emit a signal in the presence of the selective conditions, while cells which do not express the reporter gene will not emit a signal.

After treatment with the appropriate selective conditions for a suitable period of time, the number of living or surviving cells (or the number or intensity of cells emitting a reporter signal) is quantified, for example by counting the number of cells in a dish or well, or by counting the number or size of colonies in a dish or well. Control cells, which can include cells which have been treated to repress expression of the selectable marker and exposed to the selective conditions, but which have not been exposed to the test compound, are also quantified. A change in the relative number of live cells which have been treated with the test compound as compared to the relative number of cells which have not been treated with the test compound identifies the compound as an inhibitor of gene silencing. If the selectable marker is a negative selectable marker (such as HPRT or APRT), a decrease (such as a decrease of at least 10%, at least 20%, at least 50%, or even at least 95%) in the relative number of live cells as compared to the relative number of cells not treated with the compound will identify the test compound as an inhibitor of gene silencing. If the selectable marker is a positive selectable marker (such as an antibiotic resistance gene), an increase (such as an increase of at least 10%, at least 20%, at least 50%, at least 95%, or more) in the relative number of live cells as compared to the relative number of cells not treated with the compound will identify the test compound as an inhibitor of gene silencing. If the selectable marker is a reporter gene (such as luciferase or green fluorescent protein) an increase (such as an increase of at least 10%, at least 20%, at least 50%, at least 95%, or more) in the relative number of cells producing a signal (such as luminescence or fluorescence) as compared to the relative number of cells not treated with the compound will identify the test compound as an inhibitor of gene silencing.

Also disclosed herein are methods of identifying an inhibitor of gene silencing as described above, wherein the cells expressing the repressible selectable marker are part of a transgenic mouse. Repression of the selectable marker gene may include treatment of the transgenic mouse with conditions that repress expression of the gene within the mouse cells. In one example, at least some cells of the transgenic mouse express Aprt under the control of a tet-repressible promoter and a tet-responsive transcription activator. Expression of the Aprt gene may be repressed by treatment of the transgenic mouse with tet or a tet analog (such as doxycycline) for a suitable period of time (such as about 3 days to about 3 weeks). In other examples, at least some cells of the transgenic mouse express Aprt under the control of a mammalian repressible promoter (such as a tumor suppressor promoter, for example, BRCA1 or MLH1). Expression of the Aprt gene may be repressed by treatment of the transgenic mouse with conditions that repress the mammalian promoter, such as placement of the mouse cells within a hypoxic environment (such as growth of cells in a hypoxic atmosphere or in a hypoxic tumor environment) or exposure to metal ions (such as iron sulfate, cobalt chloride, or nickel chloride).

Following repression of expression of the selectable marker, the transgenic mice are administered one or more test compounds (such as 1, 2, 3, 4, 5, 6, 7, 8, 9 or 10 test compounds) which are candidate inhibitors of gene silencing. Any form of administration known in the art can be used, such as parenteral injection or infusion (such as intravenous, intramuscular, subcutaneous, or intraperitoneal injection), dermal adsorption, inhalation, or oral (e.g., by feeding). For example, the test compound can be introduced in the food or drinking water for a suitable period of time, such as about 1 day to about 3 weeks, for example, about 3 days to about 10 days, or about 7 days. In other examples, the transgenic mouse may be treated with the test compound for longer periods of time, such as two weeks, three weeks, one month, three months, six months, 12 months, or even for the life span of the mouse. The amount of test compound administered to the transgenic mice is an amount that inhibits gene silencing, such as about 1 nM to about 1 mM, for example, about 1 nM to about 100 µM, about 10 nM to about 10 µM, or about 100 nM to about 1 µM. In other examples, the test compound may be administered to the mouse at concentrations of about 0.1 mg/kg to about 100 mg/kg, such as about 1 mg/kg, 5 mg/kg, 10 mg/kg, 20 mg/kg, or 50 mg/kg. In one example, the test compound includes sulforaphane, which may be administered in amounts of about 100 mg/kg to about 1 g/kg of food, such as about 400 mg/kg to about 800 mg/kg of food. In other examples, the test compound may be a food or a food extract, which may be administered as a diet or a diet supplement (such as about 1% to about 50% of the diet, such as about 10% to about 30% of the diet). In one particular example, the test compound includes broccoli sprouts, comprising about 10% of the diet. The amount of test compound that inhibits gene silencing may vary depending on the particular compound and can be determined experimentally. For example, an appropriate dose may be determined by treating cells with a range of concentrations, and determining an $LD_{50}$ or $IC_{50}$ for the inhibition of gene silencing.

In the disclosed methods, the transgenic mice are treated with conditions that repress expression of the selectable marker for a period of time prior to treatment with the candidate compound. For example, the mice may be treated with conditions that repress selectable marker gene expression for about 1 day to about three weeks (such as about 3 days, about 5 days, about one week, about two weeks, or about three weeks) in order to repress expression, and in some instances to induce gene silencing. The test compound is then administered to the mice for a period of time (such as about one day to about three weeks, for example about one week to about two weeks), to inhibit gene silencing. In some examples, the transgenic mouse may be treated with the test compound for longer periods of time, such as one month, three months, six months, 12 months, or even for the life span of the mouse. In other examples, the conditions that repress expression of the selectable marker and administration of the test compound may be concurrent. In additional examples, the conditions that repress expression of the selectable marker may be immediately prior to administration of the test compound or the test compound can be administered prior to conditions that repress gene expression and then maintained during the time of gene repression. In some examples, the test compound may be administered concurrently with conditions that repress selectable marker gene expression and continued for a period of time following the end of the repressive treatment (such as about one day to about one month). In one particular example, the conditions that repress expression of the selectable marker are administered to the mice for seven days. On the seventh day, the test compound is administered to the mice, simultaneously with the conditions that repress selectable marker expression.

In particular examples, the transgenic mouse cells expressing the selectable marker are isolated from the transgenic mouse and characterized as to expression of the selectable marker gene. Tissues (such as kidney, lung, mammary gland, prostate, skin, or intestine) are isolated from the transgenic mice which have undergone treatment to repress expression and/or induce gene silencing of the selectable marker. Cells are isolated and grown in cell culture under selective conditions which are appropriate for the selectable marker that is expressed in the cells. In one example, when the selectable marker is Aprt, the cells are grown in the presence of a suitable concentration of 2,6-diaminopurine (DAP). Cells which express Aprt will die in the presence of DAP, while cells which do not express Aprt (such as when Aprt is silenced) will live in the presence of DAP.

After treatment with the appropriate selective conditions for a suitable period of time, the number of living or surviving cells is quantified, for example by counting the number of cells in a dish or well, or by counting the number or size of colonies in a dish or well. Control cells, which can include cells from transgenic mice which have been treated to repress expression of the selectable marker and exposed to the selective conditions, but which have not been exposed to the test compound, are also quantified. A change in the relative number of live cells which have been treated with the test compound as compared to the relative number of cells which have not been treated with the test compound identifies the compound as an inhibitor of gene silencing. If the selectable marker is Aprt, a decrease (such as a decrease of at least 20%, at least 30%, at least 50%, at least 75%, or at least 95%) in the relative number of live cells as compared to the relative number of cells not treated with the compound will identify the test compound as an inhibitor of gene silencing.

HDAC inhibitors and DNA methylation inhibitors reactivate expression of silenced genes (see, .e.g., Mund et al., *Epigenetics* 1:7-13, 2006; Kim et al., *Epigenetics* 1:14-23, 2006). The methods disclosed herein may be used to identify compounds that prevent gene silencing, or prevent re-silencing of a reactivated gene. Thus, in some examples, the disclosed cells or transgenic mice are treated with two or more test compounds, in which at least one test compound is a known HDAC inhibitor or a known inhibitor of DNA methylation and at least one additional compound is a candidate inhibitor of gene silencing. In particular examples, the cells are treated with 5-Aza-dC and one or more additional test compounds. In additional examples, the cells are treated with TSA and one or more additional test compounds. In still further examples, the cells are treated with 5-Aza-dC, TSA, and one or more additional test compounds.

Genes that have been re-activated following gene silencing (for example, by treatment with an HDAC inhibitor or DNA methylation inhibitor) frequently show unstable gene expression and undergo re-silencing, in which gene expression is lost again. In additional examples, the disclosed methods may be used to identify an inhibitor of gene re-silencing. In a particular example, gene silencing is induced (for example, by repression of gene expression, such as a selectable marker, as described above). Cells which have undergone re-activation of the gene, for example, spontaneously, or following treatment with an inhibitor of DNA methylation (such as 5-Aza-dC) or an HDAC inhibitor (such as TSA) are selected. Cells with the re-activated gene are subsequently treated with one or more test compounds (such as 1, 2, 3, 4, 5, 6, 7, 8, 9, or 10 test compounds) which are candidate inhibitors of gene re-silencing and cells are treated under selective conditions (as above) to determine the frequency of re-silencing. In some examples, the cells are treated with a test compound and a DNA methylation inhibitor (such as azacytidine or 5-aza-dC). If the selective conditions are negative selection (such as if the selectable marker is HPRT or APRT), a decrease (such as a decrease of at least 10%, at least 20%, at least 50%, or even at least 95%) in the relative number of live cells as compared to the relative number of cells not treated with the test compound will identify the test compound as an inhibitor of gene re-silencing. If the selective conditions are positive selection (such as if the selectable marker is an antibiotic resistance gene), an increase (such as an increase of at least 10%, at least 20%, at least 50%, at least 95%, or more) in the relative number of live cells as compared to the relative number of cells not treated with the test compound will identify the test compound as an inhibitor of gene re-silencing.

In additional examples, a test compound that is identified as an inhibitor of gene silencing or re-silencing is tested for the ability to inhibit DNA methylation or histone modifications. Methods to assess DNA methylation (for example, bisulfite sequencing) or histone modification (for example chromatin immunoprecipitation) are well known in the art. In particular examples, cells or a transgenic mouse are treated with the compound that is identified as an inhibitor of gene silencing and histone modification is assessed. A compound that reduces histone modification associated with gene silencing (such as dimethyl K9 of histone H3, dimethyl K27 of histone H3, trimethyl K27 of histone H3, or a combination of two or more thereof) or increases histone modification associated with gene expression (such as methyl K4 of histone H3, acetyl K9 of histone H3, acetyl K14 of histone H3, or a combination of two or more thereof) indicates that the test compound is an inhibitor of gene silencing. In other examples, cells or a transgenic mouse are treated with the compound that is identified as an inhibitor of gene silencing and DNA methylation is assessed. A test compound that reduces DNA methylation of the promoter region of the silenced gene is an inhibitor of gene silencing and can be selected for further evaluation.

IV. DNA Constructs

A. Promoters

The methods disclosed herein use DNA constructs that include nucleic acid sequences operably linked to promoter sequences. Methods of generating such constructs and introducing them into a cell or using them to generate transgenic non-human mammals, are routine in the art. The promoter sequences include necessary nucleic acid sequences near the start site of transcription, such as, in the case of a polymerase II type promoter, a TATA element. The disclosed promoters activate transcription of the operably linked nucleic acid sequences.

In some examples the promoter is a constitutively active promoter. A constitutively active promoter includes a promoter that activates expression of an operably linked nucleic acid sequence continuously, without subject to regulation by external signals or molecules. Constitutively active promoters activate expression of an operably linked sequence in all cells (for example, all cells in an organism, such as a mouse, or all cells in an organ or tissue, such as heart, lung, liver, kidney, muscle, mammary gland, etc.). Constitutively active promoters also activate expression of an operably linked sequence at all times (for example at all developmental stages of an organism or tissue and at all times during the life span of a particular cell). Examples of suitable constitutive promoters are well known to those of skill in the art and include those of viral origin, e.g., SV40 (early and late promoters), adenovirus major late promoter, Rous sarcoma virus (RSV) promoter, cytomegalovirus (CMV) immediate-early promoter, and major-intermediate-early (MIE) promoters. These promoters are useful in the disclosed methods because of their strength, constitutive expression and the ability to be expressed in varied cell lines. In a particular example, the constitutively active promoter is a CMV promoter. The CMV promoter is well known to those of skill in the art (see e.g., *Current Protocols in Molecular Biology*, Ausubel, John Wiley & Sons, 1994; *Molecular Cloning, A Laboratory Manual*, Sambrook et al., Cold Spring Harbor Laboratory, 2001).

In other examples, the promoter is a repressible promoter. Genes that are under the control of a repressible promoter are transcribed at levels that vary in response to the external environment. If a promoter is a repressible promoter, then the rate of transcription decreases in response to a repressor (or negative regulator). In some examples, the expression of a polynucleotide sequence operably linked to the promoter is reduced or prevented by a repressor, such as a drug, analyte, cofactor, regulatory protein, metal ion, or environmental condition. In particular examples, transcription of a sequence operably linked to a repressible promoter is reduced by a repressor molecule that binds to a transcription activator protein and prevents transcription from the repressible promoter.

In some examples, the repressible promoter is an exogenous repressible promoter. An exogenous promoter is one that is not of the same origin as the cells or organism in which it is present. For example, the tet-repressible promoter, which is derived in part from *E. coli*, is an exogenous promoter when it is present in mouse cell lines or a transgenic mouse. Examples of exogenous repressible promoters include the tet-repressible promoter and the Gal4-repressible promoter. In a particular example, the exogenous repressible promoter is a tet-repressible promoter. Tet-repressible promoters are well known to those of skill in the art, and are commercially available (such as the pTRE-tight vector, Clontech, Mountain View, Calif.).

In some examples, transcription from a tet-repressible promoter is reduced or prevented in the presence of tet or a tet analog (such as doxycycline). Tet (or an analog thereof) binds to a tet-responsive transcription activator and blocks its binding to the tet-responsive elements in the tet-repressible promoter, thereby blocking expression of the selectable marker gene linked to the promoter. In some examples of the disclosed method, the tet analog is doxycycline (Dox). The cells are treated with about 1 nM to about 100 µM Dox, such as about 100 nM to about 10 µM, for example about 1 µM Dox, to repress gene expression from the tet-repressible promoter. In order to repress expression from the tet-repressible promoter, cells are treated with tet or a tet analog, such as dox for about 1 day to about 3 weeks, such as about 3 days to about 2 weeks, about 5 days to 1 week, for example, 1 week. In some examples, transgenic mice which contain transgenic cells including a tet-repressible promoter are treated with about 0.2 µg/ml to about 2.0 µg/ml, such as about 1 µg/ml Dox (for example in the drinking water), to reduce or prevent transcription of the marker gene. The transgenic mice are treated with Dox for about 1 day to about 3 months, such as about 1 week, about 2 weeks, about 1 month, about 2 months, or about 3 months.

In some examples, the methods disclosed herein utilize a repressible promoter that is a mammalian repressible promoter. A mammalian promoter is one that is native to at least one mammal (for example, human or other primate, mouse, rat, cow, horse, or chicken). For example, the mouse BRCA1 promoter is a mammalian promoter that can be used in mouse cell lines (such as mouse P19 embryonal carcinoma cells) or in a transgenic mouse, while a human BRCA1 promoter is also a mammalian promoter that can be used in human cell lines (such as cells deficient in HPRT, for example, WI-L2-729HF2 cell line (ATCC CRL-8062), BUC cell line (Huff & Ishizaka, *Proc. Natl. Acad. Sci. USA* 81:1514-1518, 1984)). In additional examples, a mammalian promoter may be used in cells that originate from another organism (such as a human BRCA1 promoter used in mouse cell lines (such as a mouse P19 embryonal carcinoma cell line) or a transgenic mouse, or a mouse BRCA1 promoter used in human cell lines).

Inhibitors of gene silencing are of particular interest for the prevention or treatment of diseases associated with gene silencing, such as cancer. In particular examples, the repressible promoter is associated with cancer, such as a tumor suppressor promoter. In some examples, the selected promoter is associated with a particular cancer or type of tumor (such as breast cancer, small cell lung carcinoma or other lung cancer, colon cancer, prostate cancer, kidney cancer, melanoma, leukemia, lymphoma, glioblastoma, etc.). Examples of mammalian repressible promoters associated with cancer include, but are not limited to promoters of tumor suppressor genes that are repressible by hypoxia, estrogen, and/or metals (such as promoters from the BRCA1, MLH1, E-cadherin, estrogen receptor α, or androgen receptor genes). In some examples, the mammalian repressible promoters are repressible by nickel (such as promoters from the Mcp1, Zac1, Gas1, and Serpin genes). In a particular example, the mammalian repressible promoter is a BRCA1 promoter (such as approximately 218 immediately upstream of the transcription start site of a BRCA1 gene). Exemplary BRCA1 gene sequences are publicly available. Human BRCA1 sequences including sequences upstream of the transcription start site include (but are not limited to) Genbank Accession Nos. NC_000017.9, AC135721.4, AF284812.1, AF093485.1, AY093489.1, AY706911.1, CH471152.1, DQ299305.1, L78833.1, U61268.1, and U37574.1. Mouse Brca1 sequences including sequences upstream of the transcription start site include (but are not limited to) Genbank Accession Nos. NC_000077.5, NM_009764.2, AL590996.12, CH466558.1, U32585.1, and U33835.1.

In some examples, transcription from an endogenous repressible promoter is reduced or prevented by environmental conditions (for example, hypoxic conditions, such as placing cells in a environment of about 95% nitrogen/5% oxygen for about one to three weeks) or the presence of metal ions (such as nickel, cobalt, chromium, iron, or arsenic). In some examples, cells are grown in medium containing a metal salt, such as iron sulfate, nickel chloride, or cobalt chloride. Metal salts are included at concentrations of about 10 µM to about 1 mM for about 1 day to about three weeks. In further examples, the cells may be exposed to other known carcinogens that can inhibit gene expression (for example, benzo[a]pyrene (Jeffy et al., *Mol. Carcinog.*, 26:100-118, 1999), which inhibits BRCA1 expression).

B. Selectable Markers

The methods disclosed herein utilize a selectable marker to identify cells in which gene silencing has occurred or in which gene silencing has been significantly reduced or inhibited. In some examples, the selectable marker is expressed in mammalian cells under the control of a repressible promoter and gene silencing is induced by repressing expression of the selectable marker.

In some examples, the selectable marker is one that can be used for negative selection, such that cells which express the selectable marker die in the presence of the selective agent, while cells that do not express the selectable marker, or express it at reduced levels, live in the presence of the selective agent. A negative selectable marker refers to a gene encoding a product that can be used to selectively kill and/or inhibit growth of cells under certain conditions (such as in the presence of a drug or analyte). Selectable markers that can be used for negative selection are well known to those of skill in the art. Examples of negative selectable markers include HPRT, APRT, thymidine kinase, xanthine-guanine phosphoribosyltransferase, or adenine deaminase. Negative selection markers may also include genes encoding various toxins (including the diphtheria toxin, the tetanus toxin, the cholera toxin and the pertussis toxin). Selectable marker genes for negative selection are well known to those of skill in the art. Exemplary human HPRT sequences are publicly available (see e.g., Genbank Accession Nos. NC_000023 (133421923.133462362), AC004383.1, AY780550.1 (genomic sequences); NM_000194.1, BC000578.2, CR407645.1, M31642.1 (cDNA sequences); and NP_000185.1, AAV31777.1, AAH00578.1, CAG28573.1, AAA52690.1 (amino acid sequences)). Exemplary mouse Aprt sequences are also publicly available (see e.g. Genbank Accession Nos. NC_000074.5 (125098537.125100807), AC114917.2, CH466525.1, M86439.1 (genomic sequences); NM_009698.2, AB033539.1, AK002350.1, BC005667.1 (cDNA sequences); and NP_033828.2, EDL11691.1, AAA37256.1, BAB22029.1, AAH05667.1 (amino acid sequences)).

The cells are grown under selective conditions which are appropriate for the negative selection marker. For example, when the selectable marker is hypoxanthine-guanine phosphoribosyltransferase (HPRT), the cells are grown in the presence of a suitable concentration of 6-thioguanine (TG). Cells which express HPRT will die in the presence of TG, while cells which do not express HPRT (such as when HPRT is silenced) will live in the presence of TG (for example, about 1 µg/ml to 20 µg/ml, such as about 2.5 µg/ml to 10 µg/ml). In some examples, cells are grown in the presence of TG for about 3 days to 3 weeks, such as about 5 days to 2 weeks, about 10 days to 18 days, or about 1 week. Likewise, when the selectable marker is adenine phosphoribosyltransferase (APRT), the cells are grown in the presence of a suitable concentration of 2,6-diaminopurine (DAP) (for example about 10 µg/ml to 100 µg/ml, such as about 40 µg/ml to 80 µg/ml). Cells which express APRT will die in the presence of DAP, while cells which do not express APRT (such as when APRT is silenced) will live in the presence of DAP. In some examples, cells are grown in the presence of DAP for about 3 days to 3 weeks, such as about 5 days to 2 weeks, about 10 days to 18 days, or about 1 week. In another example, the selectable marker may be thymidine kinase (TK) and the selective conditions include growing the cells in the presence of a suitable concentration of ganciclovir or trifluorothymidine (for example, about 1 µg/ml to 25 µg/ml of trifluorothymidine). Cells which express TK will die in the presence of trifluorothymidine (or ganciclovir), while cells which do not express TK will live in the presence of trifluorothymidine (or ganciclovir). In some examples, cells are grown in the presence of trifluorothymidine (or ganciclovir) for about 3 days to 3 weeks, such as about 5 days to 2 weeks, about 10 days to 18 days, or about 1 week.

In other examples, the selectable marker is one that can be used for positive selection, such that cells which express the selectable marker live in the presence of the selective agent, while cells which do not express the selectable marker, or express it at reduced levels, die in the presence of the selective agent. A positive selectable marker refers to a gene encoding a product that can be used to selectively allow the growth of cells under certain conditions (such as in the presence of a drug or analyte, such as an antibiotic). Selectable markers that can be used for negative selection are well known to those of skill in the art. Examples of positive selectable markers are well known in the art and include antibiotic resistance genes, such as ampicillin resistance gene (β-lactamase), neomycin resistance gene (NptII), hygromycin resistance gene (Hph), kanamycin resistance gene (Kanr), puromycin resistance gene (Pac), and blasticidin S resistance gene (Bsr).

Cells are grown under selective conditions which are appropriate for the positive selection marker. For example, when the selectable marker is neomycin resistance gene NptII, the cells are grown in the presence of a suitable concentration of neomycin or a neomycin analog, such as G418. Cells which express NptII will live in the presence of neomycin or G418, while cells which do not express NptII (such as when NptII is silenced) will die in the presence of neomycin or G418. In some examples, cells are grown in the presence of G418 for about 3 days to 3 weeks, such as about 5 days to 2 weeks, about 10 days to 18 days, or about 1 week. G418 is added to the cell culture medium at a concentration of about 100 µg/ml to about 1 mg/ml, such as about 250 µg/ml to about 500 µg/ml.

In additional examples, the selectable marker may be a reporter gene, such as luciferase or a green fluorescent protein (GFP). Rather than killing the cell (as with a negative selection marker) or allowing the cell to live (as with a positive selection marker), a reporter gene provides a quantifiable signal when the gene product is expressed. Thus, in the case of luciferase, if the protein is expressed, light will be emitted in the presence of an appropriate substrate (such as luciferin). Likewise, in the case of a GFP (such as a green fluorescent protein, or variant thereof, such as yellow fluorescent protein or red fluorescent protein), if the protein is expressed a particular wavelength of light will be emitted if the protein is exposed to light at the appropriate excitation wavelength.

C. Transcription Activators

A transcription activator is a protein that binds to DNA and stimulates transcription of nearby genes. These molecules bind to specific sequences on DNA within the promoters of genes they regulate, and function by recruiting the general transcriptional initiation complex to the site where transcription of DNA into messenger RNA begins. Transcription activators have an activation domain and a DNA binding domain; some activators also have dimerization and ligand binding domains.

In a particular example, a transcription activator is a tet-responsive transcription activator (tTA) which is a chimeric protein comprising a tet-responsive factor linked to an activation domain of a herpes simplex virus transcriptional activator VP-16. The tTA binds to a tet-responsive element in a tet-repressible promoter via the tet-responsive factor. The transcriptional activator VP-16 recruits the transcription machinery and activates transcription of the operably linked gene. Tet-responsive transcription activators, such as those described are well known to those of skill in the art, and are commercially available (such as pTet-Off vectors, Clontech, Mountain View, Calif.).

In another example, a transcription activator is a GAL4 protein. GAL4 binds specifically to a cis-element within a promoter, termed the upstream activating sequence for galactose ($UAS_G$). The GAL4-linked gene is repressed when galactose is absent, but is strongly and rapidly induced by the presence of galactose. GAL4 is prevented from activating transcription when galactose is absent by the regulatory protein GAL80. GAL80 binds directly to GAL4 and likely functions by preventing interaction between GAL4 activation domains and the general transcriptional initiation factors. In the presence of galactose, transcription of a GAL4-linked gene is induced.

V. Test Compounds

The methods disclosed herein include treating cells in which gene expression has been repressed and/or gene silencing has been induced with at least one test compound to determine if the test compound is an inhibitor of gene silencing or re-silencing. In some examples the cells are treated with one or more test compounds (such as one, two, three, four, five, ten, or twenty). The test compound may be part of a mixture which includes other test compounds or additional components, such as solvents, diluents, pharmaceutically acceptable carriers, emulsifiers, salts, or other components. In some examples, the test compound may be part of a food or food extract.

Essentially any compound can be used as a potential inhibitor of gene silencing in the methods disclosed herein, although compounds that can be dissolved in water or organic solvents (such as dimethyl sulfoxide) are used in some examples. In some examples, the test compounds are a combinatorial chemical library that includes a large number of potential therapeutic compounds (such as peptides or other small organic molecules). These compounds are screened using the methods described herein to identify those that display a desired characteristic (such as inhibition of gene silencing or re-silencing). The identified compounds can serve as lead compounds for identification of related compounds with similar characteristics or can be used themselves as potential or actual therapies.

A "test compound" is any substance or any combination of substances that is useful for achieving an end or result; for example, a substance or combination of substances useful for inhibiting gene silencing or re-silencing. Any test compound that has potential (whether or not ultimately realized) to inhibit gene silencing or re-silencing is contemplated for use in the screening methods of this disclosure.

Exemplary test compounds include, but are not limited to, peptides such as, for example, soluble peptides, including but not limited to members of random peptide libraries (see, e.g., Lam et al., *Nature*, 354:82-84, 1991; Houghten et al., *Nature*, 354:84-86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., *Cell*, 72:767-778, 1993), antibodies (including, but not limited to, polyclonal, monoclonal, humanized, anti-idiotypic, chimeric or single chain antibodies, and Fab, $F(ab')_2$ and Fab expression library fragments, and epitope-binding fragments thereof), small organic or inorganic molecules (such as, so-called natural products or members of chemical combinatorial libraries), molecular complexes (such as protein complexes), or nucleic acids.

Libraries (such as combinatorial chemical libraries) useful in the disclosed methods include, but are not limited to, peptide libraries (see, e.g., U.S. Pat. No. 5,010,175; Furka, *Int. J. Pept. Prot. Res.*, 37:487-493, 1991; Houghton et al., *Nature*, 354:84-88, 1991; PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Natl. Acad. Sci. USA*, 90:6909-6913, 1993), vinylogous polypeptides (Hagihara et al., *J. Am. Chem. Soc.*, 114:6568, 1992), nonpeptidal peptidomimetics with glucose scaffolding (Hirschmann et al., *J. Am. Chem. Soc.*, 114:9217-9218, 1992), analogous organic syntheses of small compound libraries (Chen et al., *J. Am. Chem. Soc.*, 116:2661, 1994), oligocarbamates (Cho et al., *Science*, 261: 1303, 1003), and/or peptidyl phosphonates (Campbell et al., *J. Org. Chem.*, 59:658, 1994), nucleic acid libraries (see Sambrook et al. *Molecular Cloning, A Laboratory Manual*, Cold Springs Harbor Press, N.Y., 1989; Ausubel et al., *Current Protocols in Molecular Biology*, Green Publishing Associates and Wiley Interscience, N.Y., 1989), peptide nucleic acid libraries (see, e.g., U.S. Pat. No. 5,539,083), antibody libraries (see, e.g., Vaughn et al., *Nat. Biotechnol.*, 14:309-314, 1996; PCT App. No. PCT/US96/10287), carbohydrate libraries (see, e.g., Liang et al., *Science*, 274:1520-1522, 1996; U.S. Pat. No. 5,593,853), small organic molecule libraries (see, e.g., benzodiazepines, Baum, C&EN, January 18, page 33, 1993; isoprenoids, U.S. Pat. No. 5,569,588; thiazolidionones and methathiazones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514) and the like.

Libraries useful for the disclosed screening methods can be produce in a variety of manners including, but not limited to, spatially arrayed multipin peptide synthesis (Geysen et al., *Proc. Natl. Acad. Sci.*, 81(13):3998-4002, 1984), "tea bag" peptide synthesis (Houghten *Proc. Natl. Acad. Sci.*, 82(15): 5131-5135, 1985), phage display (Scott and Smith, *Science*, 249:386-390, 1990), spot or disc synthesis (Dittrich et al., *Bioorg. Med. Chem. Lett.*, 8(17):2351-2356, 1998), or split and mix solid phase synthesis on beads (Furka et al., *Int. J. Pept. Protein Res.*, 37(6):487-493, 1991; Lam et al., *Chem. Rev.*, 97(2):411-448, 1997). Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one convenient embodiment, high throughput screening methods involve providing a combinatorial chemical or peptide library containing a large number of potential inhibitors of gene silencing. Such combinatorial libraries are then screened in one or more assays as described herein to identify those library members (particularly chemical species or subclasses) that display a desired characteristic activity (such as inhibition of gene silencing). The compounds thus identified can serve as conventional "lead compounds" or can themselves be used as potential or actual therapeutics. In some instances, pools of candidate agents may be identified and further screened to determine which individual or subpools of agents in the collective have a desired activity.

In particular examples, the test compounds are inhibitors of histone deacetylases (HDAC). Examples of HDAC inhibitors include, but are not limited to short-chain fatty acids (for example, sodium butyrate, valproic acid, and phenylacetate), epoxides (for example, depudecin and trapoxin), cyclic peptides (for example, apicidin and depsipeptide), hydroxamic acids (for example, trichostatin A (TSA), suberoylanilide hydroxamic acid (SAHA), oxamflatin, scriptaid, pyroxamide, LAQ824, LBH589, and PXD101), benzamides (for example, MS-275 and CI-994), and other hybrid compounds (for example, cyclic hydroxamic-acid-containing peptides (CHAPs) and SK-7068). In a particular example, the HDAC inhibitor includes sulforaphane.

In additional particular examples, the test compounds are inhibitors of DNA methylation. Examples of DNA methylation inhibitors include, but are not limited to inhibitors of DNA methyltransferase (such as 5-aza-2'-deoxycytidine (decitabine); zebularine; azacytidine; 2-(1,3-dioxo-1,3-dihydro-2H-isoindol-2-yl)-3-(1H-indol-3-yl)propionic acid (RG108); hydralazine; (−)-epigallocatechin-3-gallate; procainamide; and). In a specific example, the DNA methylation inhibitor includes azacytidine, 5-aza-2'-deoxycytidine or zebularine.

In further examples, the test compound includes one or more HDAC inhibitors and one or more DNA methylation inhibitors. For example, the test compound may include trichostatin A and 5' aza-2'-deoxycytidine.

In some examples, the methods disclosed herein include treating cells which are part of a transgenic mouse with a test compound to identify if the test compound is an inhibitor of gene silencing. The test compounds may be administered to the mice by any suitable route, including in the diet, drinking water, or by other routes (such as parenteral injection, dermal adsorption, or inhalation). In some examples, the test compound is administered in the diet, for example a food or food additive. In a particular example the test compound is administered in the form of broccoli, broccoli sprouts, or a broccoli extract or powder. In some examples, the test compound may be sulforaphane.

VI. Transgenic Mice

Disclosed herein are methods of identifying inhibitors of gene silencing or re-silencing utilizing transgenic mice. In some examples, the method is essentially that described above, except that the cells expressing the selectable marker which are utilized in the method are part of a transgenic mouse, rather than being isolated cells in culture. In some examples, the cells are treated with the test compound by administering the test compound to the transgenic mouse, for example in the drinking water, the diet, or by another route (such as by parenteral injection, dermal adsorption, or inhalation).

In some examples, the cells expressing the selectable marker include a repressible promoter operably linked to a nucleic acid sequence encoding the selectable marker. In a particular example, the selectable marker is Aprt and in some examples, the repressible promoter is an exogenous promoter, such as a tet-repressible promoter. In other examples, the repressible promoter is a mammalian promoter, such as a mouse or human BRCA1, MLH1, E-cadherin, estrogen receptor a promoter. In some examples, the promoter is a mouse Mcp1, Zac1, Gas1, and Serpin promoter. In further examples, such as when the repressible promoter is an exogenous promoter the transgenic mouse further comprises a second nucleic acid comprising a constitutively active promoter operably linked to a transcription activator protein which activates the expression of Aprt (for example, a tet-responsive transcription activator).

Also disclosed are transgenic mice, comprising a transgenic cell, wherein the transgenic cell includes a nucleic acid including a repressible promoter operably linked to Aprt. In some examples, a nucleic acid that includes a repressible promoter operably linked to Aprt is stably introduced to the transgenic cell by homologous recombination in mouse embryonic stem (ES) cells. Methods of homologous recombination in mouse ES cells are well known to those of skill in the art (see, e.g., *Manipulating the Mouse Embryo: A Laboratory Manual*, Nagy et al., 3$^{rd}$ ed., Cold Spring Harbor Laboratory Press, 2003). When the transgenic cell is generated by homologous recombination, the promoter of the endogenous Aprt gene is replaced with a repressible promoter. In some examples, the repressible promoter is an exogenous promoter, such as a tet-repressible promoter. In other examples, the repressible promoter is a mammalian repressible promoter, such as a tumor suppressor promoter (for example aBRCA1, MLH1, E-cadherin, estrogen receptor α, or androgen receptor promoter).

In additional examples, the transgenic mouse has transgenic cells which also have a second nucleic acid comprising a constitutively active promoter operably linked to a transcription activator protein, wherein the transcription activator activates expression of APRT. In some examples the transcription activator is a tet-responsive factor fused to an activation domain of a herpes simplex virus transcriptional activator VP-16. In particular examples, the second nucleic acid comprising a transcription activator protein is stably introduced in the ES cells which comprise the repressible promoter linked to Aprt by homologous recombination. In one particular example, the transgenic mouse comprises transgenic cells which comprise a tet-repressible promoter operably linked to Aprt and a tet-responsive transcription activator operably linked to a constitutively active promoter.

VII. Cell Lines

The methods disclosed herein may be used with any suitable mammalian cell line, such as a human cancer cell line, for example those available from American Type Culture Collection (Manassas, Va.). In some examples, the cell line may include kidney, mammary epithelium, prostate, intestine, T cell, or lung cell lines. In one example, the cell line is a mouse P19 embryonal carcinoma cell line. In a particular example, the P19 cell line does not express endogenous Aprt or Hprt (Turker et al, *Somat. Cell Molec. Genet.*, 17:151-157, 1991).

Also disclosed herein is a differentiated version of the mouse P19 embryonal carcinoma cell line termed DIF6 that is stably transfected with a tet-responsive transcription activator protein operably linked to a constitutive promoter and a selectable marker operably linked to a tet-repressible promoter. The DIF6 cell line was isolated from the P19 cells by cloning a spontaneously differentiated cell (Turker et al, *Somat. Cell Molec. Genet.*, 17:151-157, 1991). In some examples, the selectable marker includes HPRT, APRT, TK, or GPT. In a particular example, the selectable marker is HPRT. In further examples, the transcription activator protein is a tet-responsive factor fused to an activation domain of a herpes simplex virus transcriptional activator VP16. Also disclosed differentiated versions of a mouse P19 embryonal carcinoma cell line (such as DIF6) stably transfected with a mammalian repressible promoter (such as a BRCA1, MLH1, E-CAD, ERα, or Mcp1 promoter) operably linked to a selectable marker gene.

In additional examples, cells for use in the methods disclosed herein include primary cell lines, such as cell lines derived from various tissues of an animal (such as a mouse, for example a transgenic mouse described in Section VI, above). In particular examples, the cells include kidney epithelial cells, mammary epithelial cells, lung alveolar cells, skin or ear fibroblast cells, prostate cells, or intestinal epithelium cells.

The present disclosure is illustrated by the following non-limiting Examples.

EXAMPLES

Example 1

Generation of Cells Expressing HPRT under Control of the Tet-off System

This example describes the generation of differentiated mouse cells which express the HPRT gene under the control of a tet-repressible promoter.

A cellular based assay was created in which expression of the selectable human HPRT cDNA was under the control of the tetracycline off (tet-off) repressible system ($P_{tet}$) (FIG. 1). Differentiated mouse cells (DIF6) that lack HPRT expression (Turker et al, *Somat. Cell Molec. Genet.*, 17:151-157, 1991.) were used. The HPRT deficient DIF6 cells were selected with 10 µg/ml 6-thioguanine (TG), which rapidly kills HPRT-expressing cells.

The construct expressing the tTA activating protein (FIG. 1A) was first introduced into the DIF6 cells by electroporation (Turker et al, *Somat. Cell Molec. Genet.*, 17:151-157, 1991). The tTA construct was the pTet-Off vector (Clontech, Mountain View, Calif.), which contains a cDNA encoding a fusion protein with a tet-responsive element binding domain, a VP16 activating domain, and a polyA splice site, all under the control of a CMV promoter. Cells stably expressing tTA were identified by selecting for expression of the linked neo-mycin resistance bacterial gene with 500 µg/ml G418.

Figure 1B:
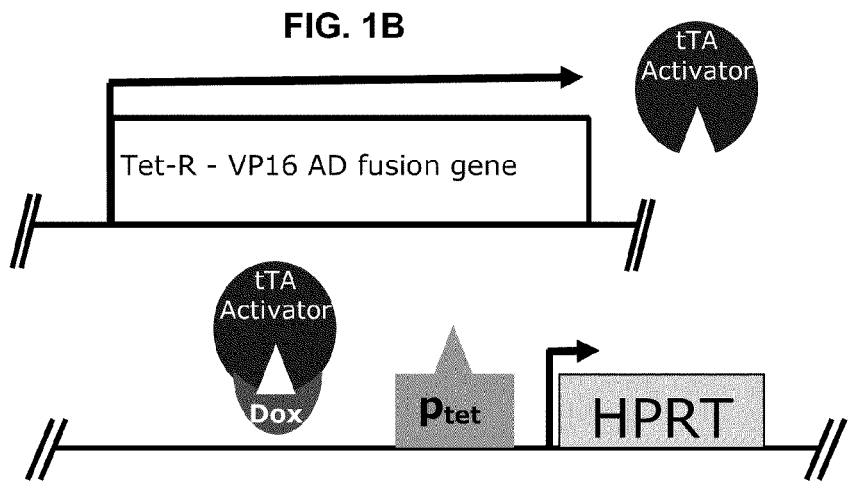
FIG. 1B shows that doxycycline (Dox) binds the activator protein to reduce HPRT expression by preventing binding of tTA to the promoter.
Figure 1C:
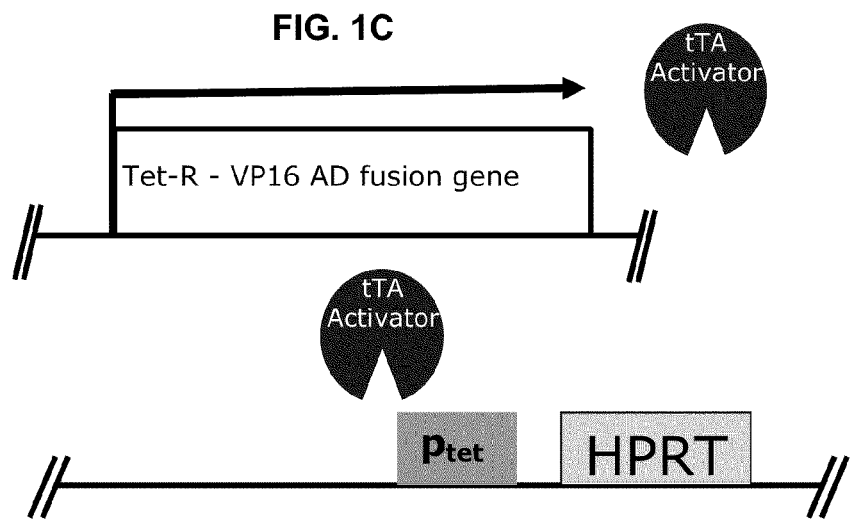
FIG. 1C shows that transient repression via Dox is predicted to lead to silencing, represented by an inability of tTA to bind to $P_{tet}$ in the absence of Dox because the tet binding sites are no longer accessible to bind the tTA protein.

Next, the construct containing P,—HPRT was introduced by electroporation into the tTA expressing DIF6 cells. The tet responsive promoter ($P_{tet}$) is included on a pTRE-Tight vector (Clontech, Mountain View, Calif.). This construct contains a tet-responsive element (TRE) that is comprised of seven direct repeats of the tet operator, which binds the tet repressor domain encoded by the pTet-OFF construct. The TRE also includes a minimal CMV promoter element. The TRE is located from positions 1-323 on the pTRE-Tight construct. The HPRT gene was inserted in the multiple cloning site located at position 323. Cells expressing $P_{tet}$-HPRT were selected in Dulbecco's Modified Eagle's Medium (DMEM) containing hypoxanthine (10 µg/ml) and azaserine (10 µg/ml), which requires HPRT expression for cell survival. A second construct expressing the bacterial puromycin resistance gene was introduced into the cells at the same time and in most cases integrated near $P_{tet}$-HPRT. Selection was performed with a concentration of 1.5 µg/ml puromycin. With the tet-off system, HPRT expression from the $P_{tet}$ promoter was repressible by adding doxycycline (Dox, a tet analog) to the medium (FIG. 1B) and expression was restored when Dox is removed (FIG. 1A). The silencing hypothesis predicts that chromatin changes occurring during gene repression will stabilize in a fraction of cells, thereby preventing the activating protein from binding to the tet repressible promoter, and hence cause silencing (FIG. 1C), which is manifested by lack of HPRT expression even after Dox is removed from the medium.

Example 2

Induction of Gene Silencing by Transient Reduction of Gene Expression

This example demonstrates that gene silencing can be induced by transient reduction or loss of gene expression.

The cell lines described in Example 1 were used to determine if gene silencing can be induced by transient reduction of gene expression. HPRT mRNA was reduced significantly in the presence of 1 µM Dox, but not completely because some mRNA was still detectable with qRT-PCR. Moreover, cells were still sensitive to TG even in the presence of Dox, which demonstrates the presence of HPRT protein. These results demonstrate that gene repression, as opposed to simple lack of gene activation, occurs in the presence of Dox. In other words, Dox can reduce but not eliminate gene expression. HPRT mRNA was restored to the original levels observed in the absence of Dox within 2 days after Dox was removed from the medium.

Figure 2:
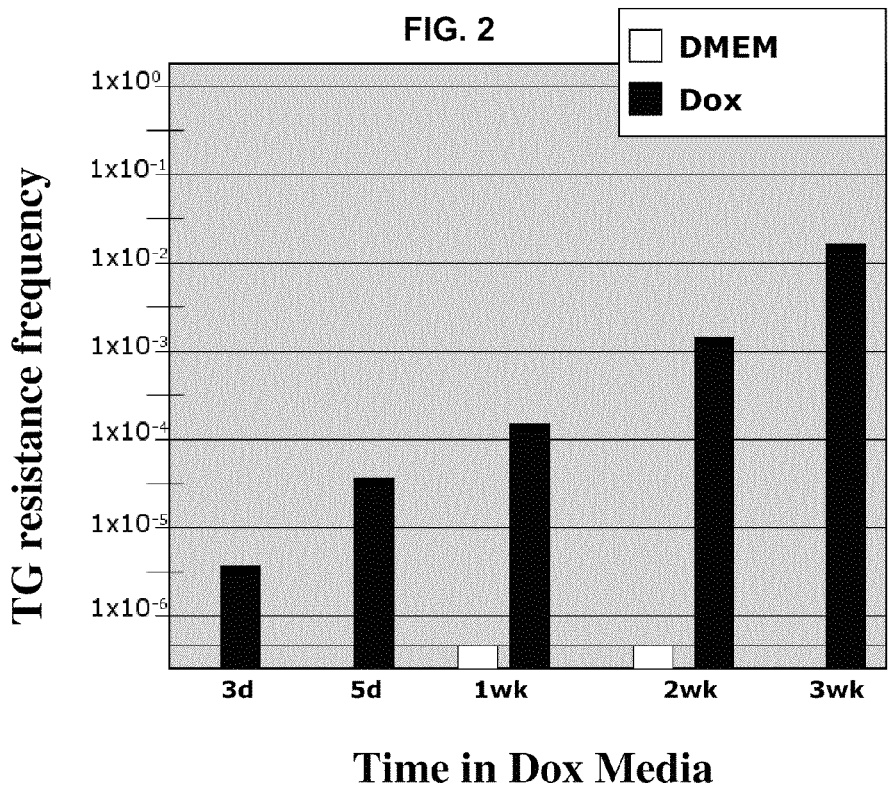
FIG. 2 is a bar graph showing silencing frequency as a function of time of Dox exposure. HPRT 3 cells with $P_{tet}$-HPRT were exposed to 1 μM Dox for the times indicated before being released from Dox and selected with 6-thioguanine (TG). TG resistance frequencies are plotted. No TG resistant clones were identified after one or two weeks of growth in medium without Dox. The HPRT 3 cell line was created by inserting the $P_{tet}$-HPRT construct and the tet-responsive transcription activator construct into the genome of a mouse cell line termed DIF6.

To determine if gene repression could induce silencing, three cell lines expressing HPRT under control of the $P_{tet}$ promoter ($P_{tet}$-HPRT) were exposed to Dox for 7 days and then selected with TG in the absence of Dox. These cells lines were chosen because 1) each gave few or no spontaneous TG resistant clones and 2) $P_{tet}$-HPRT was integrated near the bacterial puromycin (pur) selectable gene, which allowed puromycin selection to be used to prevent deletion of $P_{tet}$-HPRT. The results from a typical experiment (Table 1) show that TG resistant clones arose as a result of transient reduction in $P_{tet}$-HPRT expression from Dox exposure. For this experiment, $1\times10^6$ cells were exposed to 1 µM Dox for 7 days, the Dox was removed from the medium, the cells re-plated in 100 mm dishes at a density of $1\times10^5$ cells per dish and exposed to TG (5 µg/ml) and puromycin (1.5 µg/ml). TG selected for cells that became HPRT deficient from silencing and puromycin selection ensured that that deletion of $P_{tet}$-HPRT did not provide an alternative pathway for TG resistance. A time course experiment in which the cells were exposed to Dox for periods ranging from 3 days to 3 weeks showed a time dependent increase in the frequency of TG resistant clones (FIG. 2).

TABLE 1

Induction of silencing via repression of $P_{tet}$-HPRT in HPRT3 cell line

| Cell Line | Treatment | Silencing Frequency |
| --- | --- | --- |
| HPRT 1 | Untreated | $9.8 \times 10^{-6}$ |
| HPRT 1 | 1 µM Dox (7 days) | $9.4 \times 10^{-3}$ |
| HPRT 3 | Untreated | $<4.5 \times 10^{-6}$ |
| HPRT 3 | 1 µM Dox (7 days) | $2.1 \times 10^{-4}$ |
| HPRT 4 | Untreated | $<4.4 \times 10^{-6}$ |
| HPRT 4 | 1 µM Dox (7 days) | $1.6 \times 10^{-4}$ |

Example 3

Confirmation that Repression of HPRT Expression Leads to Epigenetic Silencing

This example confirms that transient repression of gene expression leads to epigenetic gene silencing, as opposed to gene mutation, as demonstrated by spontaneous reversal of silencing of after treatment of the cells with inhibitors of DNA methylation and histone deacetylation.

Having demonstrated that transient loss of HPRT expression induced TG resistant clones (as shown in Example 2), the next question was whether these clones arose from epigenetic silencing of $P_{tet}$-HPRT. One indication that HPRT silencing occurred, as opposed to mutation, was the observation that spontaneous revertants arose at high frequencies from the TG resistant clones (Table 2). HPRT revertants were identified by their ability to grow in medium containing hypoxanthine and azaserine (HAz medium) because only cells expressing HPRT can survive in this medium. High frequency reversion is characteristic of silencing (Turker et al., *Somat. Cell Mol. Genet.* 10:55-69, 1984), and inconsistent with mutation (Turker, *Mutagenesis* 18:1-6, 2003).

TABLE 2

Spontaneous reversion frequencies for TG resistant clones induced by gene repression.

| TG Cell Line | Spontaneous Reversion Frequency |
|---|---|
| HPRT 1-TG-1* | <0.4 × $10^{-6}$ |
| HPRT 1-Dox-TG2 | 5.1 × $10^{-3}$ |
| HPRT 1-Dox-TG3 | 2.5 × $10^{-3}$ |
| HPRT 3-Dox-TG1 | 1.8 × $10^{-2}$ |
| HPRT 3-Dox-TG2 | 1.2 × $10^{-2}$ |
| HPRT 4-Dox-TG1 | 7.6 × $10^{-3}$ |
| HPRT 4-Dox-TG2 | 1.6 × $10^{-3}$ |

*HPRT 1-TG-1 was a spontaneous TG resistant cell line and appears to have lost HPRT expression from a mutation because no revertant cells were identified; the remaining cell lines arose after Dox exposure and readily yielded revertant cells consistent with silencing.

Figure 3:
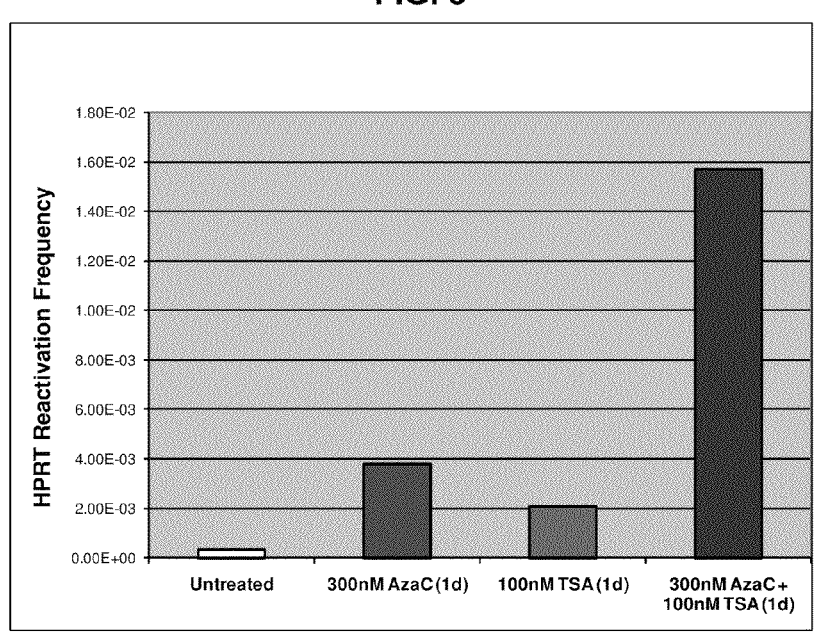
FIG. 3 is a bar graph showing HPRT reversion frequencies in H3TG3 cells. Reversion frequencies were determined for a cell line with a silenced HPRT allele after no treatment (Untreated), treatment with 300 nM 5-aza-2'-deoxycytidine (AzaC) for 24 hours, treatment with 100 nM trichostatin A (TSA) for 24 hours, or a combination of 5-Aza-dC and TSA at the same concentrations for 24 hours. Revertant cells were selected with medium containing hypoxanthine and azaserine. The H3TG3 cell line is a TG resistant version of the HPRT3 cell line (FIG. 2), created by treating the HPRT3 cell line for one week with Dox and then selecting for a TG resistant clone.

At the molecular level, tumor suppressor silencing in mammalian cells is associated with two hallmarks, chromatin hypoacetylation and promoter region DNA methylation (Palii and Robertson, *Crit. Rev. Eukaryot. Gene Expr.* 17:295-316, 2007). Histone deacetylases, which are responsible for hypoacetylation, are inhibited by trichostatin A (TSA). TSA was therefore used as a probe to determine if histone deacetylation played a significant role in the silencing phenotype. Consistent with this notion, the frequency of revertant cells increased after TSA exposure (FIG. 3). For this experiment, 1×$10^6$ cells were plated in a T-75 flask and treated with 100 nM TSA for 24 hours. After an additional 24 hour recovery time, the cells were re-plated in 100 mm dishes (1×$10^5$ cells per dish) in HAz medium to select for cells that regained HPRT expression. Likewise, the DNA methyltransferase inhibitor 5-aza-deoxycytidine (5-aza-dC) induced revertant cells, which demonstrated that DNA methylation was also present at the silenced promoter (FIG. 3). For this experiment, the cells were treated identically to those used for the TSA experiment, except they were exposed to 300 nM 5-aza-dC instead. Combined treatment with TSA and 5-Aza-dC provides a synergistic reactivation of tumor suppressor gene expression by targeting both histone deacetylation and DNA methylation, respectively (Cameron et al., *Nat. Genet.* 21:103-107, 1999). The same effect was observed when the cells were exposed simultaneously to 100 nM TSA and 300 nM 5-aza-dC (FIG. 3). Promoter region DNA methylation was confirmed with a bisulfite sequence analysis and histone deacetylation with a chromatin immunoprecipitation (ChIP) analysis. Hence the endpoints of silencing in the disclosed inducible silencing system, promoter region DNA methylation and histone deacetylation, are the same as those reported for tumor suppressor gene silencing. Therefore, the disclosed methods provide a representative model with which to trigger and then study the silencing process.

Figure 4:
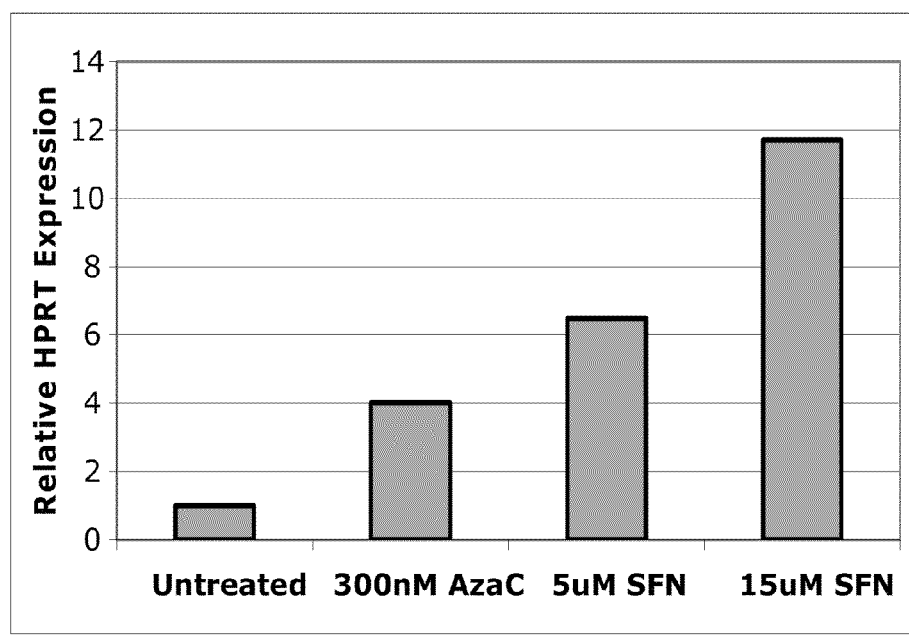
FIG. 4 is a bar graph showing reactivation of silenced HPRT following treatment with sulforaphane (SFN), an extract from broccoli sprouts. Relative levels of HPRT mRNA were determined in H3TG3 cells exposed to 300 nM 5-Aza-dC, 5 μM SFN, or 15 μM SFN for 24 hours. RNA was collected after an additional 24 hours and quantitative real time PCR (qRT-PCR) was used to determine mRNA levels, which were set to 1.0 for untreated cells.

The ability of sulforaphane (SFN) to reactivate silenced HPRT alleles in a TG resistant cell line was determined following the same protocol used above, except the cells were exposed to 5 or 15 µM SFN for 24 hours and RNA extracts were made from the cells 24 hours after the SFN exposure ended. RNA levels instead of reactivation frequencies were used as the endpoint for this experiment. As shown in FIG. 4, 24-hour SFN exposure was sufficient to reactivate the silenced HPRT allele in a dose dependent manner, and at levels greater than that for exposure with 5-aza-dC. In a separate experiment, SFN and 5-aza-dC acted synergistically, as observed for TSA when combined with 5-aza-dC.

Example 4

Inhibition of Silencing via Inhibition of Histone Deacetylation

This example shows that silencing of HPRT is reduced by treatment with an inhibitor of histone deacetylation.

Previous studies with Aprt constructs demonstrated that DNA methylation is a secondary step in the silencing process, which indicates that chromatin change occurs first (Yates et al, *Mol. Cell. Biol.*, 23, 4461-4470, 2003). If so, silencing should be prevented by inhibiting histone deacetylation. To test this, experiments in which silencing is induced by exposure to Dox were repeated (see Example 2), but in this case the cells were exposed to TSA for the last 24 hours of Dox exposure.

Figure 5:
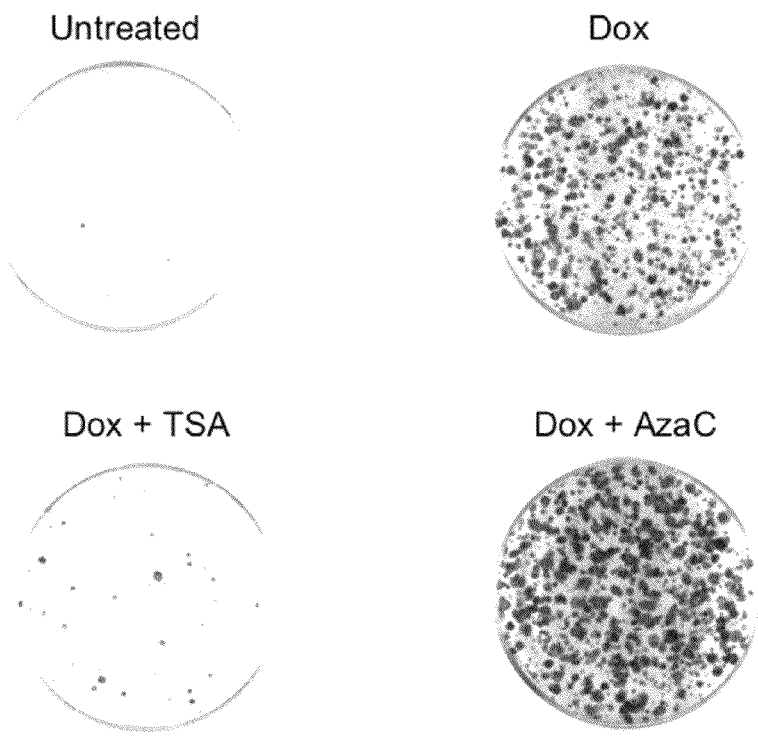
FIG. 5 is a series of digital images of dishes of TG resistant HPRT9 cells after various treatments. HPRT9 cells with $P_{tet}$-HPRT were exposed to 1 μM Dox for 7 days (Dox) to induce HPRT silencing. Some cells were also exposed 100 nM TSA (Dox+TSA) or 300 nM 5-Aza-dC (Dox+AzaC) on day 7 of Dox treatment. Control (Untreated) cells were not exposed to Dox, TSA, or 5-Aza-dC. $1 \times 10^5$ cells were plated per dish in TG medium and the dishes were stained after 12 days. The dark circles depict clones of cells that survived TG selection (TG resistant cells).
Figure 6:
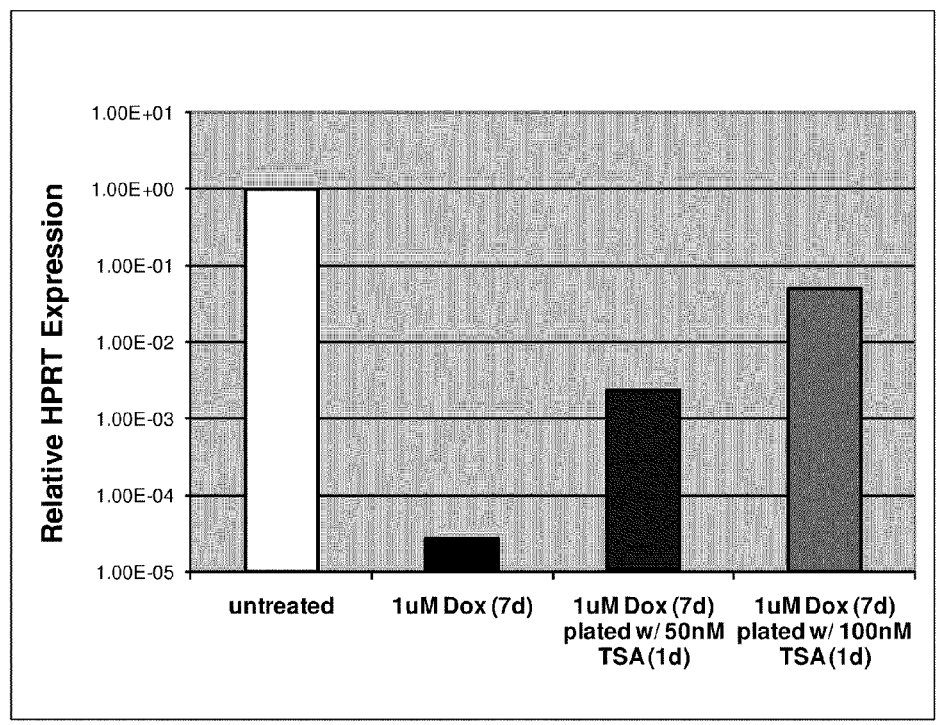
FIG. 6 is a bar graph showing relative HPRT expression after Dox exposed HPRT3 cells were treated with TSA. The HPRT3 cells expressing $P_{tet}$-HPRT were treated with 1 μM Dox for 6 days and on day 7 some cells were exposed to both Dox and TSA (at concentrations shown). RNA was collected at the end of the 7th day and assayed for HPRT levels with qRT-PCR.

The results showed that the 24-hour TSA exposure significantly inhibited the induction of cells with silenced HPRT alleles (FIG. 5). In contrast, the DNA methylation inhibitor, 5-Aza-dC, did not inhibit the induction of silencing. Moreover, TSA exposure restored a level of HPRT expression (FIG. 6), suggesting that maintenance of an open chromatin confirmation allowed additional tTA activating protein to bind to the $P_{tet}$ promoter despite the presence of Dox in the medium. Combined, these results demonstrate that a very early event in gene silencing (perhaps the earliest) is histone deacetylation, that inhibition of histone deacetylation inhibits silencing, and DNA methylation is a secondary event.

Example 5

Induction of Gene Silencing by Hypoxia

This example shows that silencing of the BRCA1 and MLH1 promoters can be induced by hypoxia.

DIF6 cells were transformed with a construct containing a minimal human BRCA1 promoter fragment (218 bp immediately upstream from the transcription start site of human BRCA1) operably linked to the human HPRT cDNA (BRCA1-HPRT). The cells were also transformed with the puromycin gene to allow for selection for retention of BRCA1-HPRT construct when selecting for TG resistant cells. The transformed cells were selected with hypoxanthine and azaserine (10 µg/ml each) and puromycin (1.5 µg/ml) to obtain cells expressing both the BRCA1-HPRT and puromycin constructs. Similarly, DIF6 cells were transformed with a construct containing the MLH1 promoter operably linked to the human HPRT cDNA (MLH1-HPRT).

Figure 7:
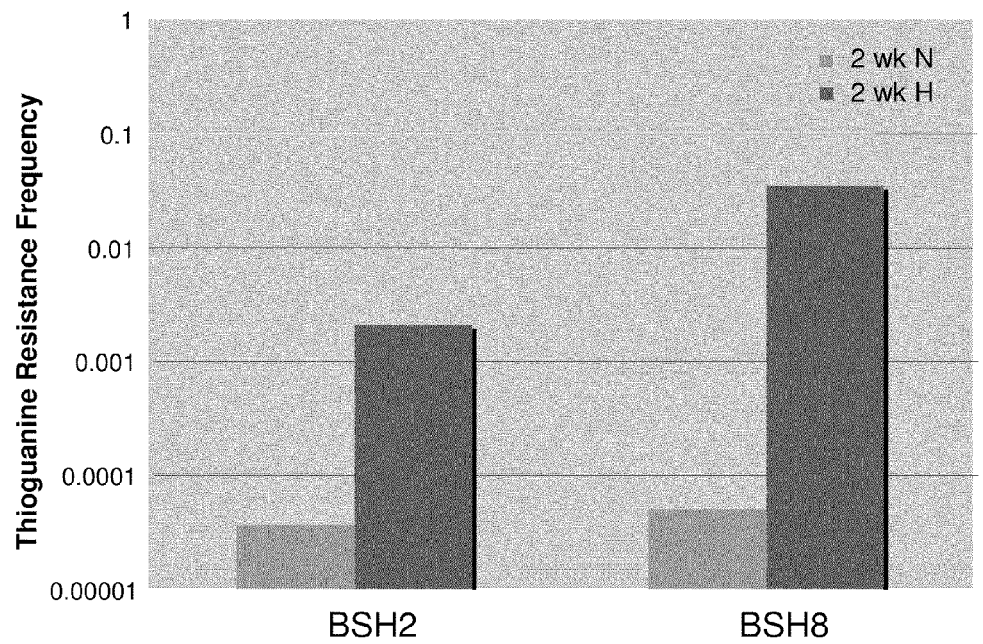
FIG. 7 is a bar graph showing relative TG resistance frequencies for cells (BSH2 and BSH8) containing the human BRCA1 promoter operably linked to HPRT cDNA after two weeks selection in normoxic (N) or hypoxic (H) conditions.

Two BRCA1-HPRT cell lines obtained with this approach (BSH2 and BSH8) were exposed to hypoxic conditions (growth in an atmosphere of about 95% nitrogen and 5% oxygen) for two weeks and then exposed to 2.5 µg/ml TG under hypoxic conditions for two additional weeks to select for TG resistant cells. FIG. 7 shows that the frequencies of TG resistant clones were approximately 10-100 times higher for the hypoxia treated BSH2 and BSH8 cells, respectively, when compared to the TG resistance frequencies in normoxic (i.e., ambient air) conditions. Once TG resistant clones arose, they did not require continued growth under hypoxic conditions to maintain TG resistance. Thus, the resistance phenotype became independent of hypoxia.

Figure 8:
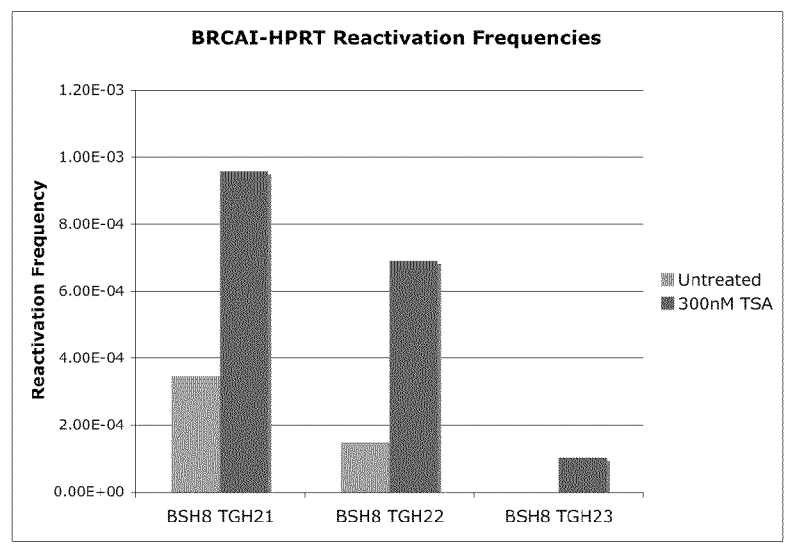
FIG. 8 is a bar graph showing reactivation frequency of BSH8 TG resistant clones treated with 300 nM TSA for 16 hours or in the absence of TSA (untreated).
Figure 9:
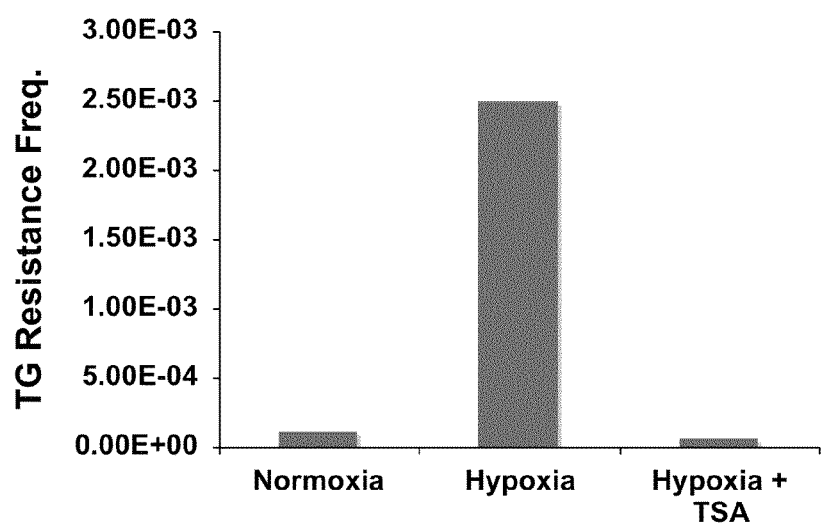
FIG. 9 is a bar graph showing TG resistance frequency for BSH8 cells exposed to normoxia or hypoxia for two weeks and then selected under normoxic conditions with TG. An aliquot of the hypoxia exposed cells was treated with TSA for 24 hours (hypoxia+TSA) prior to TG selection.

To confirm that silencing (as opposed to mutation) was induced by hypoxia exposure, several BRCA1-HRPT TG resistant clones induced by hypoxia were expanded and tested to determine if they could yield revertant cells after exposure to TSA (300 nM) as presented in Example 3 for cells with silenced $P_{tet}$-HPRT constructs. The results shown in Table 3 and FIG. 8 show that TSA induced revertant cells, demonstrating that hypoxia exposure induced silencing of the BRCA1 promoter. Consistent with that result, HPRT mRNA was reduced in the TG resistant clones and restored in TSA-induced revertants. In addition, TSA inhibited hypoxia-induced silencing (FIG. 9). However, 5-Aza-dC did not inhibit the induction of silencing, did not reactivate the silenced clones, and did not show DNA methylation at the promoter. These results are consistent with a role for histone deacetylation, but not DNA methylation, in hypoxia-induced silencing of the BRCA1 promoter.

TABLE 3

Spontaneous and TSA-induced reversion frequencies for TG resistant clones containing the BRCA1-HPRT construct.

| TG Cell Line | Spontaneous Reversion Frequency | TSA-Induced Reversion Frequency |
|---|---|---|
| BSH8TG22 | $1.5 \times 10^{-4}$ | $6.9 \times 10^{-4}$ |
| BSH8TG23 | $<0.5 \times 10^{-6}$ | $1.0 \times 10^{-4}$ |

A MLH1-HPRT transfected cell line was exposed to normoxic or hypoxic conditions for 72 hours. Hypoxia repressed expression of HPRT and induced TG resistant clones. Thus, hypoxic conditions induced gene silencing of both BRCA1 and MLH1 promoter-driven HPRT expression.

Example 6

Induction of Gene Repression or Gene Silencing by Metal Ions

This example demonstrates that silencing of the BRCA1 promoter and repression of the MLH1 and Mcp1 promoters can be induced by exposure to metal ions.

Figure 10A:
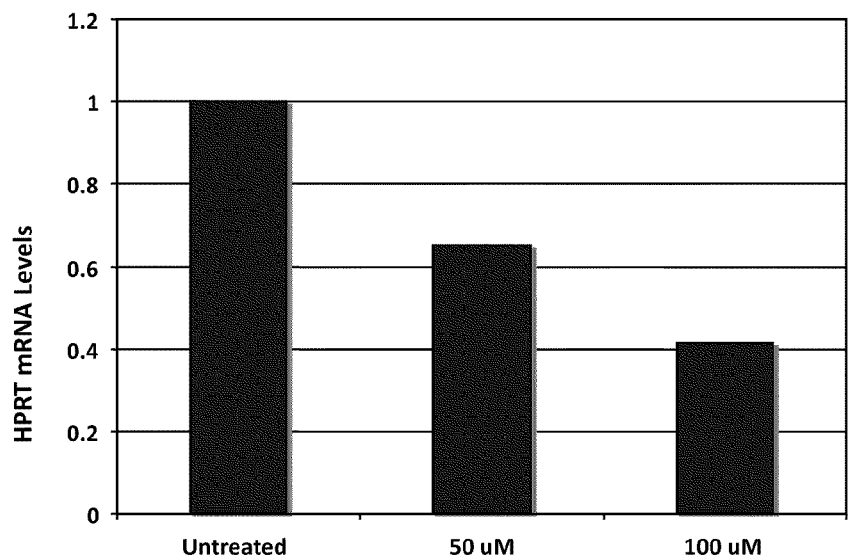
FIG. 10A is a bar graph showing HPRT mRNA levels (normalized to GAPDH) in BRCA1-HPRT transfectants exposed to 50 μM or 100 μM $CoCl_2$ for two weeks.
Figure 10B:
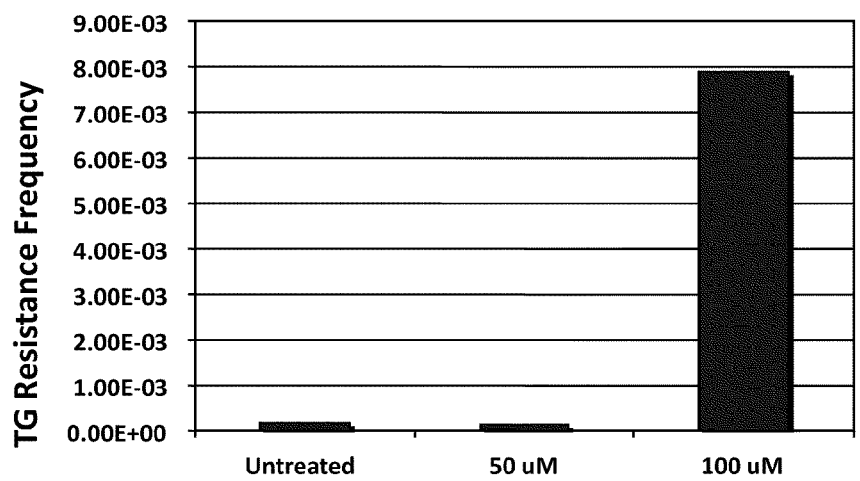
FIG. 10B is a bar graph showing TG resistance frequency for BRCA1-HPRT transfectants exposed to 50 μM or 100 μM $CoCl_2$ for two weeks, followed by TG selection.

BRCA1-HPRT and MLH1-HPRT cell lines as described in Example 5 were exposed to $CoCl_2$ for two weeks, followed by selection of TG resistant clones. BRCA1-HPRT expression was repressed in a dose-dependent manner by $CoCl_2$ exposure (FIG. 10A). However, TG-resistant clones only arose in BRCA1-HPRT cells exposed to 100 μM $CoCl_2$ (FIG. 10B), suggesting a possible threshold for gene repression-induced silencing by exposure to metal ions. Expression from the MLH1 promoter was also repressed by exposure to $CoCl_2$.

DIF6 cells transfected with MLH1-HPRT or Mcp1-HPRT constructs were also exposed to varying concentrations of $NiCl_2$ for 48 hours. Nickel exposure resulted in a dose-dependent repression of HPRT expression.

Example 7

Aprt Alleles that are Silenced and Reactivated are Unstable

This example describes isolation of cell lines with unstably reactivated Aprt alleles and the role of DNA methylation and histone modification in the silencing and reactivation of the mouse Aprt gene.
Methods
Mouse embryonal cell lines P19H22, D3, D7, and D3S1 were cultured as described previously (Turker et al., *Somat. Cell Mol. Biol.* 17:151-157, 1991). P19H22 cells contain a single copy of Aprt derived from the C3H mouse strain (Turker et al., *Mutat. Res.* 329:97-105, 1995). The D3, D7, and D3S1 cell lines were maintained in the presence of 80 μg/ml 2'-6-diaminopurine (DAP) unless otherwise indicated and contain an inactive Aprt allele. These cell lines were derived from P19H22.

Bisulfite sequencing to determine DNA methylation for regions containing the Aprt promoter and 470 bp of upstream sequence in the D3, D7, D3S1, and P19H22 cells included CpGs between −498 and +60 was performed as previously described (e.g., Yates et al., *J. Biol. Chem.* 274:36357-36361, 1999). Genomic DNA was isolated from cell cultures using DNAzol (Molecular Research Center, Cincinnati, Ohio) according to the manufacturer's instructions. For each treatment, 2-4 μg of genomic DNA was digested with BsrI restriction enzyme. Digested genomic DNA was modified in a solution of 6.24 M urea, 4 M sodium bisulfite, and 10 mM hydroquinone as described previously (Yates et al., *Mol. Cell. Biol.* 23:4461-4470, 2003). PCR amplification of modified DNA, cloning of PCR products, and sequence analysis were also described previously (Yates et al., *J. Biol. Chem.* 274: 36357-36361, 1999), with the following exceptions. The primers used in the initial PCR reaction were the sense primer H2+S 5'-GAG GAG GGT ATA TTT TGT TGT AAT G-3' (SEQ ID NO: 1) and the antisense primer ACA+29 5'-AAA AAC AAA AAA AAA ATA AAT ATC AAC AC-3' (SEQ ID NO: 2). PCR product from this initial reaction was used as input in a second reaction with the nested sense primer H2+NS23 5'-AGT GTT TGT GGT TTT AGA GAA GG-3' (SEQ ID NO: 3) and the antisense primer ACA+29. PCR products were cloned using Strataclone™ PCR cloning kit (Stratagene, La Jolla, Calif.). Sequencing analysis showed all cytosine bases not present in the CpG dinucleotide context were converted to thymine indicating complete bisulfite modification of the genomic template occurred.

Total RNA was isolated from cell cultures with the RNeasy® Mini Kit (Qiagen, Valencia, Calif.) according to the manufacturer's instructions. Total RNA samples were converted to cDNA using Quantitect® Reverse Transcription Kit (Qiagen, Valencia, Calif.) with removal of genomic DNA contamination. 100 ng cDNA was used as input in subsequent quantitative-PCR analysis for either Aprt amplification across the exon 2-3 splice site with the sense primer qAprt-F 5'-CTC TTG GCC AGT CAC CTG AAG-3' (SEQ ID NO: 4), the antisense primer qAprt-R 5'-TCT AGA CCT GCG ATG TAG TCG ATC T-3' (SEQ ID NO: 5) and the TaqMan probe 5'-FAM-CAC GCA CAG CGG C-MGB-3' (SEQ ID NO: 6) or Gapdh (Mouse TaqMan Endogenous Control, Applied Biosystems) with iQ Supermix (Bio-Rad) and a Bio-Rad iCycler. Aprt results were normalized in relation to Gapdh mRNA levels and displayed relative to expression levels in P19H22 cells.

To measure Aprt reactivation, cells were plated into 100 mm culture plates at densities ranging from $1 \times 10^3$ to $1 \times 10^5$ cells per plate. The next day the medium was removed, and medium containing 10 μg/ml azaserine and 10 μg/ml adenine (AzA) was added to select for active Aprt expression. The same protocol was used to measure Aprt re-silencing, but the selective media contained 80 μg/ml DAP instead of AzA. Cells were cultured for approximately two weeks in the appropriate selective media before staining live colonies with crystal violet solution. To estimate cloning efficiencies, additional cells were plated under identical conditions as selective plates but at lower densities, 250 to 1000 cells per plate, without selection. Silencing or reactivation frequencies were calculated by dividing the number of clones growing under selection by the effective number of cells plated (as determined with the cloning efficiency plates).

Cells were treated overnight (about 16 hours) with media containing 300 nM TSA (Wako USA, Richmond, Va.) to inhibit histone deacetylation, 3 µM 5-aza-dC (Sigma-Aldrich, St. Louis, Mo.) to inhibit DNA methylation, or the combination of 300 nM TSA and 3 µM 5-aza-dC. Cells were allowed to recover 24 hours in DMEM after drug treatment before harvesting for RNA purification.

ChIP assays were carried out as described previously (Oyer et al., PLoS ONE 4:e4832, 2009). Protein-DNA complexes were immunoprecipitated with antibodies to acetyl-H3K9 (07-352, Millipore, Billerica, Mass.), mono/di/trimethyl-H3K4 (05-791, Millipore), dimethyl-H3K9 (ab1220, Abcam, Cambridge, Mass.), and trimethyl-H3K27 (17-622, Millipore). Quantitative PCR using an iCycler® and iQ™ Supermix (Bio-Rad, Hercules, Calif.) was used to analyze the immunoprecipitated DNA. The Aprt promoter was amplified and detected using the sense primer 5'-AAC GTA TGT CGA GGT AGG CGT GTA-3' (SEQ ID NO: 7), the antisense primer 5'-ATC TCC TTC ATC ACA TCT CGA G-3' (SEQ ID NO: 8), and the TaqMan probe 5'-FAM-TAC CTC CTC CCT GCC TCC TAC A-3' (SEQ ID NO: 9). The active Gapdh promoter was amplified using the sense primer 5'-TTG AGC TAG GAC TGG ATA AGC AGG-3' (SEQ ID NO: 10), the antisense primer 5'-AAG AAG ATG CGG CCG TCT CTG GAA-3' (SEQ ID NO: 11), and the TaqMan probe 5'-FAM-TAT AAA TAC GGA CTG CAG CCC TCC CT-3' (SEQ ID NO: 12). The silenced Mage-a promoter was amplified using the sense primer 5'-GTT CTA GTG TCC ATA TTG GTG-3' (SEQ ID NO: 13) and the antisense 5'-AAC TGG CAC AGC ATG GAG AC-3' (SEQ ID NO: 14), and amplification and quantitation was done using iQ SYBR Green Supermix (Bio-Rad). The specific signal from each immunoprecipitation relative to signal from input was calculated for the three promoters, Aprt, Gapdh, and Mage. For activating modifications, levels at Aprt are displayed relative to the Gapdh promoter; for the repressive modification, dimethyl-K9 H3, results are displayed relative to the Mage promoter.

Results

Figure 11:
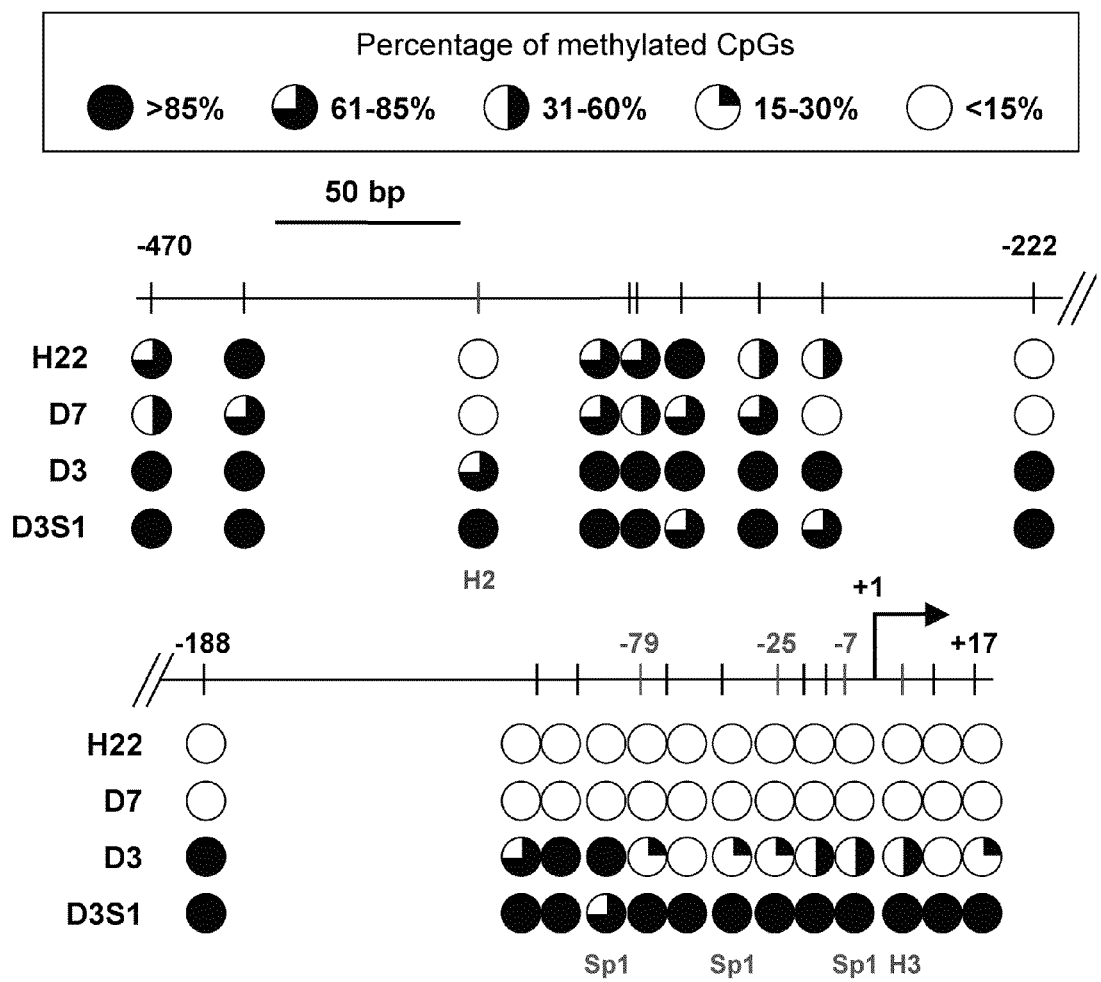
FIG. 11 is a diagram showing DNA methylation patterns of the Aprt promoter in parental P19H22 (H22) cells and cell lines with Aprt silencing (D3, D7, and D3S1). The shaded circles indicate the percentage of total alleles (n=14) that were methylated at the corresponding CpG. Base pair positions are labeled relative to the Aprt transcriptional start site (arrow marked +1). CpG sites within an Sp1 binding site (−79, −25, and −7) and CpG sites within an HpaII restriction site (H2 and H3) are indicated.
Figure 12:
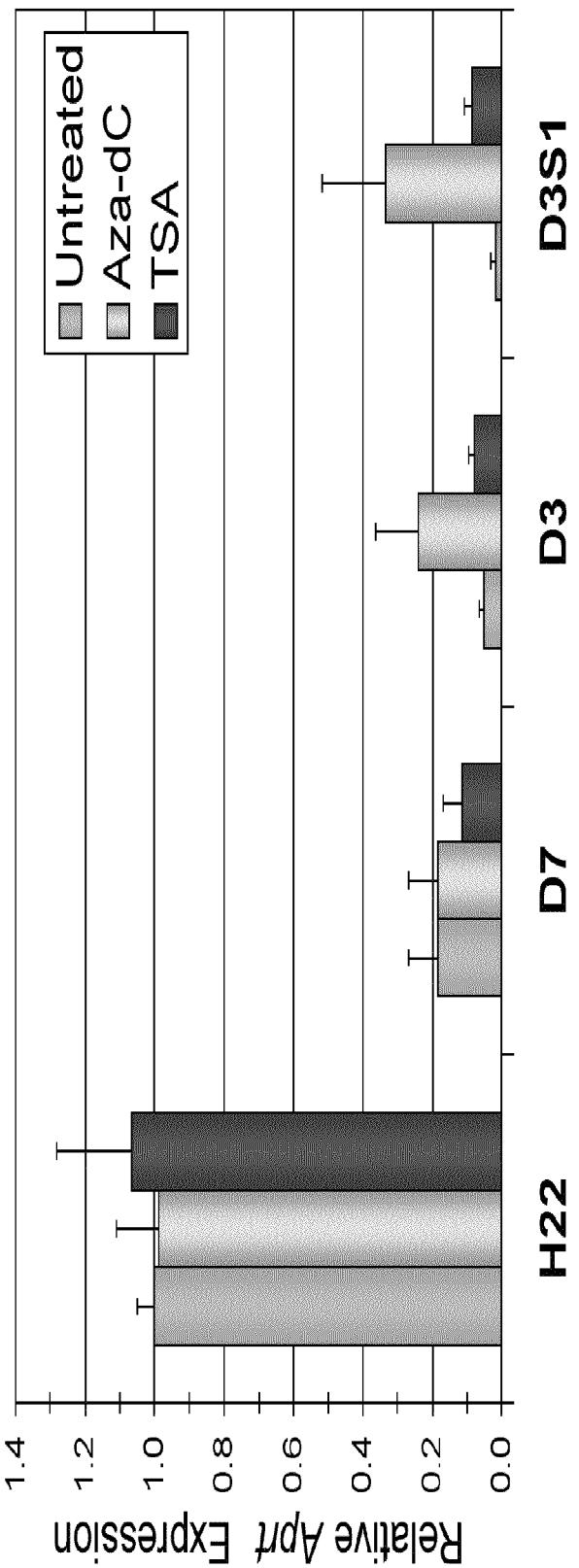
FIG. 12 is a bar graph showing relative Aprt mRNA expression in parental cells with active Aprt expression (H22) and DAP-resistant cell lines with silenced Aprt expression (D7, D3, and D3S1) in untreated cells and cells treated with 3 μM 5-aza-dC or 300 nM TSA. Results are the average of triplicate reactions with error bars indicating the standard deviation.

The mouse P19H22 embryonal carcinoma cell line contains a single expressed Aprt allele; the other allele was removed by a spontaneous deletion. Two cell lines from P19H22 with silenced Aprt alleles, D3 and D7, were previously isolated (Cooper et al., Somat. Cell Mol. Genet. 17:105-116, 1991). Bisulfite sequencing was used to measure methylation status for regions containing the Aprt promoter and 470 bp of upstream sequence in D3, D7, D3S1, and P19H22 cells. The results demonstrated no DNA methylation of the promoter region for the P19H22 cells, which express Aprt, and the same methylation pattern for the D7 cells (FIG. 11), which express Aprt at approximately ⅕ the level of P19H22 (FIG. 12). Therefore, loss of Aprt expression does not require DNA methylation. However, both the D3 and D3S1 cells exhibited Aprt promoter region DNA methylation (FIG. 11) and Aprt expression at levels less than 5% of that for P19H22 (FIG. 12). Therefore, promoter DNA methylation can accompany loss of expression.

Both cell lines, D3 and D7, spontaneously reactivated Aprt expression at very high frequencies (greater than 10%), when measured by selecting reactivant clones in medium supplemented with azaserine and adenine (AzA), which requires Aprt expression for cell survival. The lack of DNA methylation in the Aprt promoter of D7 cells and incomplete DNA methylation on many alleles in the D3 cells could account for the very high spontaneous Aprt reactivation. Spontaneous reactivation for Aprt in the D3S1 cells was lower at a level of approximately 1%.

Inhibiting DNA methylation by 5-aza-dC treatment reactivated expression in D3 and D3S1, the two cell lines with hypermethylated Aprt promoters but did not alter expression in the D7 clone, which lacked DNA hypermethylation in the Aprt promoter (FIG. 12) Inhibition of histone deacetylases by TSA treatment also had no affect on Aprt mRNA levels in the D7 cell line. By comparison, a small induction of Aprt mRNA levels was detected in the D3S1 and D3 cell lines after TSA treatment, an 8- and 1.5-fold increase, respectively, as compared to untreated cells. Although the relative fold change differed between D3 and D3S1 after TSA treatment, the absolute levels of Aprt mRNA induced by TSA treatment were approximately equal.

The bisulfite sequencing analysis identified three distinct DNA methylation patterns among the silenced cell lines, no promoter region DNA methylation (D7), variable promoter region DNA methylation (D3), and essentially complete promoter region DNA methylation (D3S1). To determine if these methylation patterns correlated with different histone modifications, a chromatin immunoprecipitation (ChIP) analysis was performed using antibodies against activating modifications, acetylation at H3K9 and methylation at H3K4, and repressive modifications, methylation at H3K9 and H3K27. Histone modifications measured at the Aprt promoter in the P19H22 cells were consistent with active expression, i.e., high levels of acetyl-K9 H3 (FIG. 13A) and methyl-K4 H3 (FIG. 13B) and low levels of dimethyl-K9 (FIG. 13C).

Figure 13B:
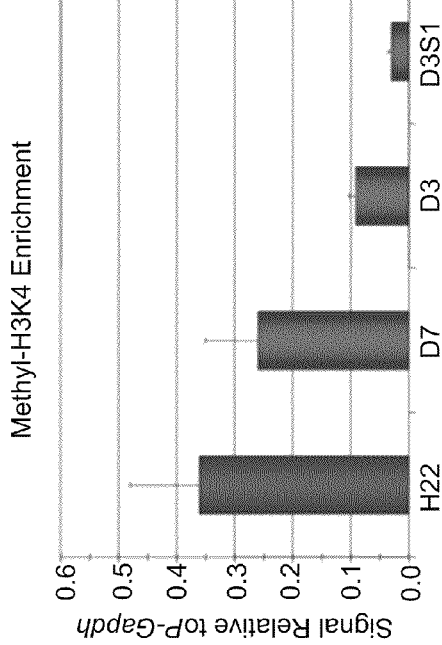
FIG. 13B shows methylation at lysine 4 of histone H3.
Figure 13D:
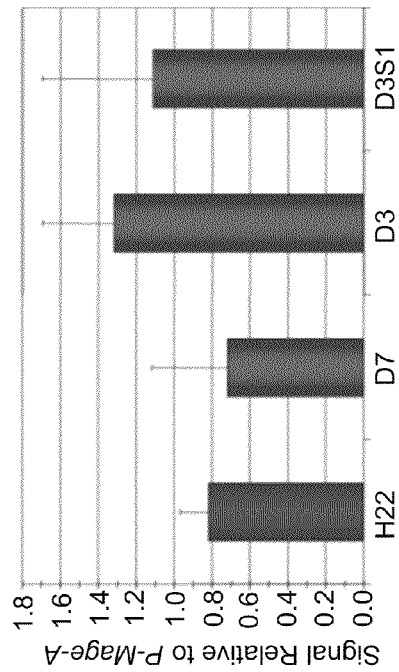
FIG. 13D shows trimethylation at lysine 27 of histone HJ. Immunoprecipitated DNA levels were measured by qRT-PCR and normalized to enrichment at either the Gapdh promoter or the Mage-a promoter.
Figure 13A:
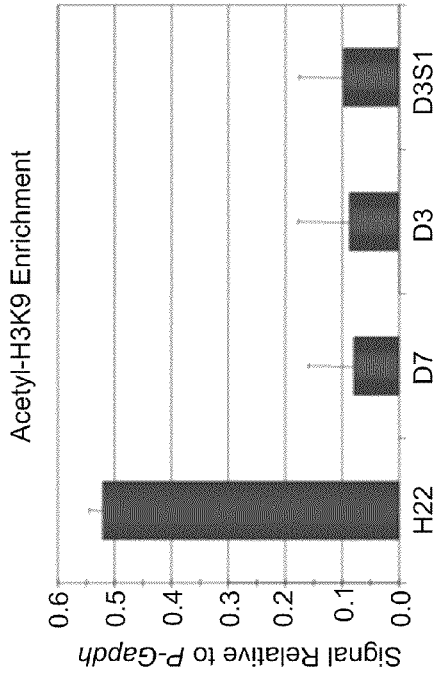
FIG. 13A shows acetylation at lysine 9 of histone H3.
Figure 13C:
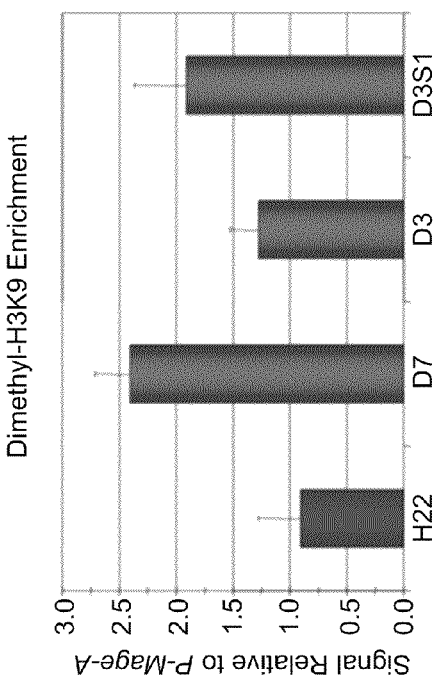
FIG. 13C shows dimethylation at lysine 9 of histone H3.

In D7 cells, which had no DNA hypermethylation at the Aprt promoter, levels of acetyl-K9 H3 were decreased, and a corresponding increase in dimethyl-K9 was observed (FIGS. 13A and 13C). However, levels of methyl-K4 H3 were comparable to those measured at the active Aprt promoter in P19H22 (FIG. 13B). Thus, the Aprt promoter in D7 cells exhibited a bivalent modification pattern with enrichment of both repressive and activating modifications. In contrast, the D3 and D3S1 clones had decreased levels of both modifications associated with active expression, i.e., acetylation at K9 and methylation at K4 of histone H3 (FIGS. 13A and B). The stably silenced D3S1 cells had higher levels of the repressive histone modification dimethyl-K9 H3 at the Aprt promoter than the D3 cell line, though both were higher than that observed in the P19H22 parental cells (FIG. 13C). Levels of trimethyl-K27 H3 were also measured at the Aprt promoter, but no significant differences were observed between P19H22 and the silenced cell lines (FIG. 13D), which indicates that this histone modification was not altered as a result of promoter silencing.

Figure 14B:
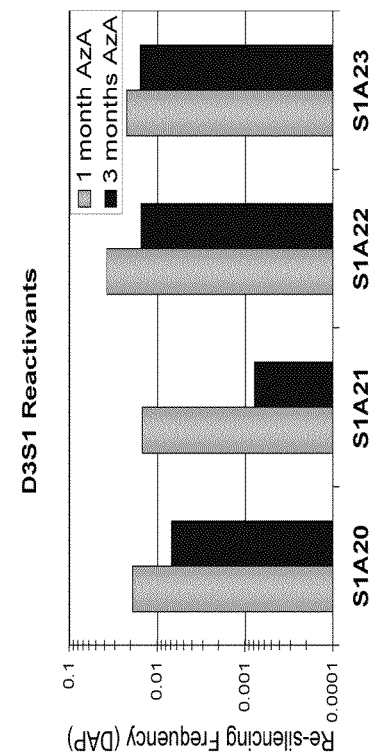
FIG. 14B shows re-silencing frequency of D3S1 cell line-derived reactivants. Re-silencing frequency was measured after reactivant clones had been growing continuously in AzA for one month or three months.
Figure 14A:
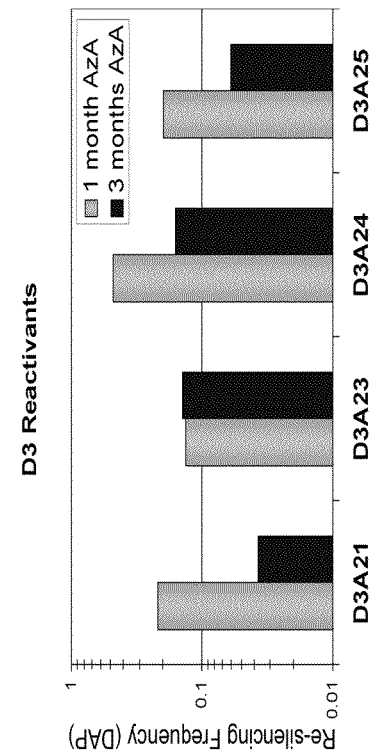
FIG. 14A shows re-silencing frequency of D3 cell line-derived reactivants.

The results comparing spontaneous reactivation of the D3 and D3S1 cell lines suggest that higher levels of promoter DNA methylation increase the stability of the epigenetic silencing because spontaneous Aprt reactivation is reduced 10-20-fold for D3S1 cells. To study the relationship between DNA methylation and promoter reactivation, re-silencing frequencies were measured for D3 and D3S1 spontaneous reactivant clones after maintaining active expression for one or three month by growth in medium with adenine and azaserine. Re-silencing frequencies were high (1 to 10%) at one month and changed little from after three months growth in medium with azaserine and adenine (FIGS. 14A and 14B). Thus, cells with reactivated but unstable Aprt alleles can be isolated to test for compounds that inhibit re-silencing.

Example 8

Inhibition of Gene Re-Silencing by HDAC Inhibition

This example describes inhibition of gene re-silencing by an inhibitor of histone deacetylase.

A DIF6 derived cell line expressing HPRT under the control of the $P_{tet}$ system was established as described in Example 1. Gene silencing was induced following repression of HPRT expression in the presence of Dox and spontaneous reactivant cell lines that grew well in AzHx medium were isolated. Re-silencing frequency was measured in the presence of the DNA methylation inhibitor 5-aza-dC or the HDAC inhibitor TSA.

Figure 15:
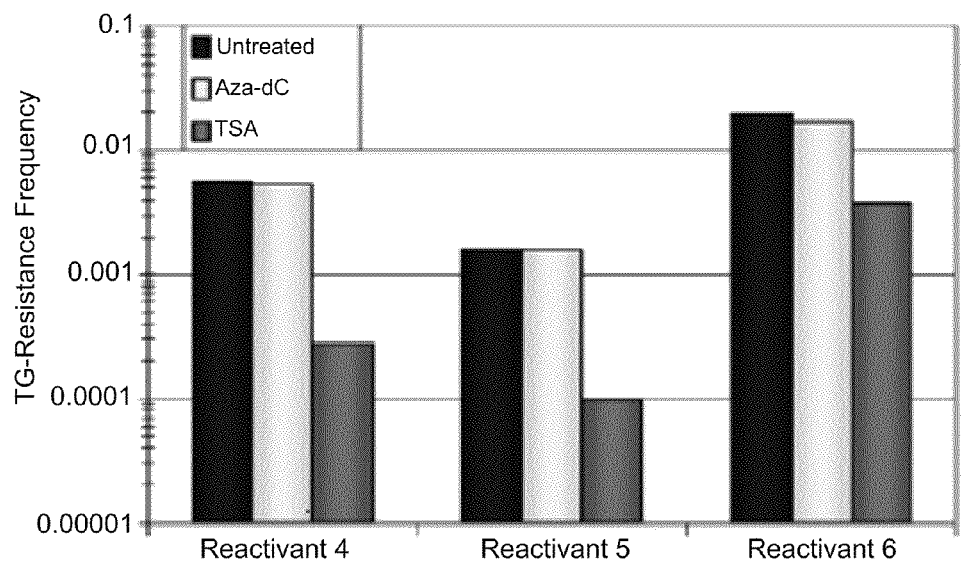
FIG. 15 is a bar graph showing inactivation frequency of H4-derived clones with silenced and reactivated HPRT expression after overnight treatment with vehicle (Untreated), 300 nM 5-aza-dC (Aza-dC) or 100 nM TSA (TSA) before selecting against HPRT activity with TG. Frequencies represent the fraction of cell colonies surviving after two weeks of TG selection.

The reactivant cell lines exhibited a high frequency of spontaneous re-silencing when treated with vehicle (FIG. 15). The re-silencing frequency was essentially unchanged in the presence of 300 nM 5-aza-dC. However, HDAC inhibition with TSA reduced the re-silencing frequency about 5- to 20-fold (FIG. 15). Thus, re-silencing was dependent on histone deacetylation, but not DNA methylation.

Example 9

Generation of a Mouse Model of Inducible Gene Silencing

This example describes the generation of a transgenic mouse that can be used as a model of inducible gene silencing.

Transgenic mice are generated which express the tTA activator protein and Aprt under the control of the tet-repressible promoter ($P_{tet}$-Aprt). The endogenous mouse Aprt allele is replaced with $P_{tet}$-Aprt via homologous recombination, providing a transgenic mouse with the appropriate number of Aprt alleles (two per diploid genome).

Figure 16:
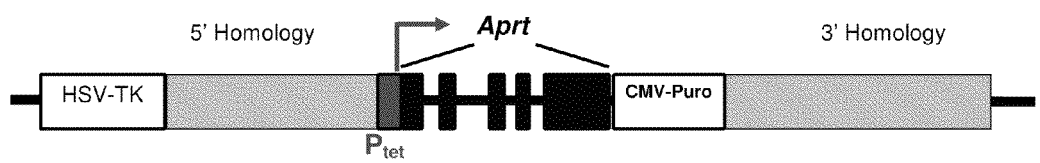
FIG. 16 is a schematic diagram of a targeting construct for replacing endogenous Aprt with an Aprt transgene controlled by the $P_{tet}$ promoter in mouse embryonic stem cells. The construct contains a $P_{tet}$ promoter (see FIG. 1), which replaces the Aprt promoter, the entire Aprt gene, 5' and 3' targeting arms (stippled), the HSV-TK gene, and the puromycin (puro) resistance gene. Different parts of the figure are not drawn to scale.

The targeting construct contains $P_{tet}$-Aprt flanked by approximately 4 kb of upstream and 4 kb downstream of Aprt region 129/Sv DNA to provide targeting arms (FIG. 16). In essence, the endogenous Aprt promoter is replaced with the $P_{tet}$ promoter. The targeting construct also has an upstream Herpes simplex virus Tk gene, which is deleted upon targeted integration leading to ganciclovir resistance, and the bacterial puromycin (pur) gene, which is used for selection of $P_{tet}$-Aprt upon integration into the ES cell genome.

A first transfection step targets the wild type Aprt allele in the ES cells derived from 129Sv mice that have one Aprt allele knocked out. Therefore, the remaining expressed Aprt allele in the ES cells is targeted. The combination of ganciclovir and puromycin resistance in transfected ES cells is consistent with targeted integration, which is confirmed with a Southern blot analysis. Ganciclovir/puromycin resistant ES clones are screened by Southern blot analysis to identify those in which targeting of the expressed Aprt allele has occurred. Successfully targeted ES cells are transiently transfected with the tTA construct to ensure that $P_{tet}$-Aprt expression occurs (measured with RT-PCR), which means it will also occur when this construct is stably transfected with the construct expressing the tTA activator protein.

A second transfection then stably introduces the tTA construct expressing the activator protein. The full cytomegalovirus promoter is used to drive tTA expression, to provide ubiquitous expression (for example, expression in all tissues) when the mouse model is made. The tTA construct is the pTet-Off vector (Clontech, Mountain View, Calif.), which contains a cDNA encoding a fusion protein with a tet-responsive element binding domain, a VP16 activating domain, and a polyA splice site, all under the control of a CMV promoter. The tTA construct is transfected into the ES cells containing targeted $P_{tet}$-Aprt and cells with integrated constructs are selected with G418 because the tTA construct contains the bacterial neo gene.

Introduction of the tTA protein activates $P_{tet}$-Aprt in the ES cells. Cells that express $P_{tet}$-Aprt at a level comparable to that for an endogenous Aprt allele are identified by first selecting for expressing clones with medium containing azaserine and adenine (AzA; selects for Aprt expressing cells) and then using qRT-PCR to measure Aprt mRNA levels. ES cells that express $P_{tet}$-Aprt at the desired level are exposed to Dox to confirm that $P_{tet}$-Aprt is repressible. Finally, candidate ES cells are differentiated into embryoid bodies, which contain the three basic cell types: mesoderm, ectoderm, and endoderm. These embryoid bodies are stained with Aprt antibody to demonstrate uniform expression of $P_{tet}$-Aprt (i.e., Aprt protein expression in all cells), which will indicate uniform expression of the tTA activating protein. This ensures uniform $P_{tet}$-Aprt expression when mice are made from the ES cells via blastocyst injection.

Once candidate ES cells are chosen, blastocyst injection is used to generate chimeric mice using routine methods (see e.g., *Manipulating the Mouse Embryo: A Laboratory Manual*, Nagy et al., $3^{rd}$ ed., Cold Spring Harbor Laboratory Press, 2003). Chimeric mice are identified by mosaic coat color and then bred with non-transgenic mice to demonstrate germ line chimerization. Pups that contain both the $P_{tet}$-Aprt and tTA activator genes, which are most likely on different chromosomes and therefore sort together in 50% of germline transmissions, are chosen for further breeding.

The transgenic mice are maintained in the 129/Sv genetic background. The founder mice (derived from the germ-line testing above) are males heterozygous for both the tTA and Ptet-Aprt constructs. They are crossed with females to obtain progeny that are heterozygous for both constructs; one in four pups from germ line transmissions should be double heterozygotes. Two rounds of breeding may be necessary to obtain double homozygotes because only 1 in 16 pups from a double heterozygous cross will be double homozygotes. Once male and female mice homozygous for both Ptet-Aprt and tTA are obtained, the strain is maintained by crossing the double homozygous mice.

Example 10

Demonstration and Characterization of Inducible Gene Silencing In Vivo

This example describes the characterization of repression of Aprt expression in a transgenic mouse expressing Aprt under the control of a tet-repressible promoter and demonstration that repression of Aprt expression leads to gene silencing in vivo.

The transgenic mice that express Ptet-Aprt ubiquitously under the control of the tTA activator protein (described in Example 9) can be used to determine conditions that repress Aprt expression maximally in different tissues. Dox at concentrations ranging from 0.2 to 2.0 µg/ml is placed in the drinking water and replaced every two to three days. RNA from mouse tissues is isolated every 5 days and tested with qRT-PCR to determine when Aprt expression stabilizes at low (i.e., repressed) levels. The mouse tissues examined include kidney, lung, ear, skin, mammary epithelium (in female mice), prostate (in male mice), intestinal epithelium, and spleen.

After conditions for Aprt repression are determined, the next step is to demonstrate inducible gene silencing in vivo. Briefly, the mice are sacrificed and cell suspensions obtained from enzymatically digested tissues. The cell suspensions are plated in medium containing 2,6-diaminopurine (DAP) at about 10 µg/ml to about 100 µg/ml for about 1-3 weeks, which selects specifically for Aprt deficient cells by killing Aprt expressing cells. Some DAP resistant cells are expanded for a molecular analysis to determine the types of events leading to Aprt deficiency.

All mice used are homozygous (i.e., biallelic) for both $P_{tet}$-Aprt and the tTA activator because biallelic mutation (i.e., simultaneous mutational loss of both alleles for an autosomal gene) does not occur at detectable frequencies (Turker, *Mutagenesis* 18:1-6, 2003). In contrast, biallelic silencing has been demonstrated for endogenous mouse Aprt (Rose et al, *Cancer Research,* 60, 3404-3408, 2000). Experiments are conducted to confirm a low or absent background frequency of DAP resistant (i.e., Aprt deficient) cells in untreated $P_{tet}$-Aprt mice (i.e., not exposed to Dox) using the same protocol.

Next, the mice are exposed continuously to the Dox concentration that represses Aprt expression maximally for variable periods of time. DAP resistant frequencies are measured at each time point for kidney, lung, ear, skin, mammary epithelium (in female mice), prostate (in male mice), and splenic T-cells to demonstrate that transient loss of Ptet-Aprt expression triggers silencing and to determine if silencing frequencies increase as a function of duration of Dox exposure, as observed in cell culture (see FIG. 2). The DAP selection dishes do not contain Dox because silenced alleles should not require the continued presence of the repressive agent.

It is expected that DAP resistant clones will appear in tissues from Dox treated mice at significantly higher frequencies than tissues from untreated mice, and that Dox-induced silencing will increase with duration of treatment.

To demonstrate silencing, some DAP resistant clones are expanded to obtain a sufficient number of cells for molecular and cellular assays commonly used to establish silencing. Parameters to be examined include: 1) reduced Aprt mRNA expression, 2) promoter region DNA methylation, 3) promoter region hypoacetylation, 4) increased mRNA expression after treating the cells with 5-aza-dC and/or TSA, and 5) the appearance of revertant cells at high frequencies after treatment of the cells with 5-aza-dC and/or TSA. Methods described in Examples 2-4 are used to determine these parameters. These parameters will confirm loss of Aprt expression from an epigenetic mechanism.

Example 11

Inhibition of Gene Silencing by SFN In Vivo

This example shows the inhibition of gene silencing in vivo by administering a diet rich in sulforaphane, which exhibits histone deacetylase activity.

Mice expressing Aprt under the control of the $P_{tet}$ promoter (Example 9) are fed unmodified or modified AIN93G diets (American Institute of Nutrition 93 growth diet (Dyets, Bethlehem, Pa.)), respectively. The modified diets contain 10% or 20% broccoli sprout extract by weight, which correspond to SFN concentrations of 400 and 800 mg/kg of food, respectively. Broccoli sprout powder (obtained from Natural Sprout LLC, Springfield, Mo.) contains approximately 4000 ppm SFN.

The SFN-enriched diet is started 7 days prior to addition of Dox to the drinking water; the SFN diet and Dox exposure runs in parallel for an amount of time sufficient for maximal induction of silencing (as determined in Example 10). Tissues from some animals are processed to confirm the presence of SFN in the target tissues and quantify the level present.

Aprt silencing frequencies are determined as described in Example 10 for control mice and mice fed broccoli sprout-enriched diet Inhibition of Aprt silencing by the broccoli sprout-enriched diet is reflected by reduced frequencies of DAP resistant clones with the in vivo assay. As a positive control for inhibition of silencing, the mice are injected with TSA (10 mg/kg) a total of 8 times (every 2-3 days) during the Dox exposure period. TSA injected mice do not receive the SFN-enriched diet.

A second approach for determining inhibition of Aprt silencing in mice fed a broccoli sprout diet is to determine Aprt mRNA levels. Cellular RNA is isolated from tissues of Dox-exposed mice that are fed or not fed SFN and qRT-PCR performed to determine if SFN inhibits the ability of Dox to repress gene expression. The inhibitory effect is examined when the mice are exposed to both SFN and Dox simultaneously, and also when the mice are exposed sequentially to Dox and then SFN. The latter experiment will determine if SFN can increase the rate of recovery of gene expression that will occur when Dox is removed from the drinking water.

Example 12

Methods of Identifying Inhibitors of Gene Silencing In vitro

This example describes exemplary methods of identification of inhibitors of gene silencing using an in vitro assay in cultured cells.

A. Exogenous Repressible Promoter

Mouse DIF6 cells which lack expression of the endogenous Hprt and Aprt (McBurney and Rogers, *Dev. Biol.,* 89:503-508, 1982) are stably transfected with a DNA construct containing the human HPRT cDNA operably linked to a tet-repressible promoter (such as HPRT cDNA cloned in the pTRE-Tight vector, Clontech, Mountain View, Calif.). The same mouse DIF6 cells which were stably transfected with the HPRT cDNA construct are stably transfected with a second DNA construct containing a tet-responsive transcription activator protein operably linked to a constitutive CMV promoter (such as the pTet-Off vector, Clontech, Mountain View, Calif.).

Following establishment of the stably transfected cell line, the cells are treated with Dox to repress expression of HPRT and induce gene silencing. The cells are treated with a range of concentrations of Dox (from about 100 nM to about 10 µM Dox) for about 5 days to 3 weeks to repress expression of HPRT and induce gene silencing.

Subsequent to (such as immediately following) or overlapping with Dox treatment (for example overlapping by at least one day), the cells are treated with one or more test compounds which are potential inhibitors of gene silencing. The cells are treated with a range of concentrations of the test compounds from about 1 nM to about 1 mM for about one day to about 3 weeks.

The cells are then grown under selective conditions to identify cells in which the test compound has inhibited gene silencing, and thereby reactivated expression of the HPRT gene. Cells are plated in medium containing about 1 µg/ml to about 20 µg/ml TG (which will kill cells which express HPRT), for about 1-3 weeks. The surviving cells are quantified by counting the number of live cells or number or size of colonies of live cells. A statistically significant decrease (such as a decrease of at least 10%, at least 50%, or at least 90%) of the number of surviving or live cells, as compared to the number of live cells from a control sample which has not been treated with the test compound, but has otherwise been treated identically, identifies the compound as an inhibitor of gene silencing.

Test compounds which are identified as inhibitors of gene silencing are further characterized, for example determining the $LD_{50}$ or $IC_{50}$ of the compound for gene silencing and further testing of the compound in an in vivo model of gene silencing.

B. Mammalian Repressible Promoter

Mouse DIF6 cells which lack expression of the endogenous Hprt and Aprt (McBurney and Rogers, *Dev. Biol.*, 89:503-508, 1982) are stably transfected with a DNA construct containing the human HPRT cDNA operably linked to a mammalian repressible promoter (such as HPRT cDNA cloned linked to a mouse or human BRCA1 promoter).

Following establishment of the stably transfected cell line, the cells are treated with conditions that repress expression of HPRT from the BRCA1 promoter and induce gene silencing. The cells are treated with hypoxic conditions (growth in an atmosphere containing about 95% nitrogen and about 5% oxygen) for about 1-2 weeks to repress expression of HPRT and induce gene silencing.

Subsequent to (such as immediately following) or overlapping with the hypoxic conditions (for example overlapping by at least one day), the cells are treated with one or more test compounds which are potential inhibitors of gene silencing. The cells are treated with a range of concentrations of the test compounds from about 1 nM to about 1 mM for about one day to about 3 weeks.

The cells are then grown under selective conditions to identify cells in which the test compound has inhibited gene silencing, and thereby reactivated expression of the HPRT gene. Cells are plated in medium containing about 1 µg/ml to about 20 µg/ml TG (which will kill cells which express HPRT), for about 1-3 weeks. The surviving cells are quantified by counting the number of live cells or number or size of colonies of live cells. A statistically significant decrease (such as a decrease of at least 10%, at least 50%, or at least 90%) of the number of surviving or live cells, as compared to the number of live cells from a control sample which has not been treated with the test compound, but has otherwise been treated identically, identifies the compound as an inhibitor of gene silencing.

Test compounds which are identified as inhibitors of gene silencing are further characterized, for example determining the $LD_{50}$ or $IC_{50}$ of the compound for gene silencing and further testing of the compound in an in vivo model of gene silencing.

Example 13

Methods of Identifying Inhibitors of Gene Silencing In vivo

This example describes identification of inhibitors of gene silencing using a transgenic mouse model of gene silencing.

A. Exogenous Repressible Promoter

Transgenic mice are generated as described in Example 9 and can be utilized for identifying inhibitors of gene silencing using the exogenous tet-repressible promoter. Repression of Aprt expression will be induced by addition of Dox at concentrations ranging from 0.2 to 2.0 µg/ml in the drinking water for about one to two weeks. Subsequent to (such as immediately following) or overlapping with the Dox administration (for example overlapping by at least one day), the mice are treated with one or more test compounds which are potential inhibitors of gene silencing. The mice are treated with a range of concentrations of the test compounds for about one day to about 3 weeks. If the test compound is administered in the drinking water, the range of concentrations is about 100 nM to about 10 µM. If the test compound is a food or food extract, it is included in the diet at about 400 mg/kg-800 mg/kg of food or about 10-30% of the diet. If the compound is administered by injection, it is injected once daily at an amount of about 1 mg/kg to about 100 mg/kg.

Following administration of the test compound, the mice are sacrificed, tissues of interest are removed (such as liver, lung, kidney, colon, mammary gland, or prostate), and cells are grown in culture. The cells are grown under selective conditions to identify cells in which the test compound has inhibited gene silencing, and thereby reactivated expression of the Aprt gene. Cells are plated in medium containing about 10 µg/ml to about 100 µg/ml DAP (which will kill cells which express Aprt), for about 1-3 weeks. The surviving cells are quantified by counting the number of live cells or number or size of colonies of live cells. A statistically significant decrease (such as a decrease of at least 10%, at least 50%, or at least 90%) of the number of surviving or live cells, as compared to the number of live cells from a control sample which has not been treated with the test compound, but has otherwise been treated identically, identifies the compound as an inhibitor of gene silencing.

Test compounds which are identified as inhibitors of gene silencing are further characterized, for example determining the dose that kills 50% of mice ($LD_{50}$) and the maximum tolerated dose.

B. Mammalian Repressible Promoter

The transgenic mice are generated as described in Example 9, except that the Aprt promoter is replaced with a mammalian repressible promoter, such as BRCA1. These transgenic mice do not express the tet-responsive transcription activator. Repression of Aprt expression is induced by conditions that repress the particular promoter that is linked to Aprt. For example, the BRCA1 promoter is repressed by treatment with benzo[a]pyrene (Jeffy et al., *Mol. Carcinog.* 26:100-118, 1999). Most promoters that are repressible by hypoxia (including the BRCA1 promoter) are also repressible by metals, such as iron, nickel, or cobalt (Maxwell and Salnikow, *Cancer Biol. Ther.*, 3:29-35, 2004).

Subsequent to (such as immediately following) or overlapping with the treatment to repress selectable marker expression (for example overlapping by at least one day), the mice are treated with one or more test compounds which are potential inhibitors of gene silencing. The mice are treated with a range of concentrations of the test compounds for about one day to about 3 weeks. If the test compound is administered in the drinking water, the range of concentrations is about 100 nM to about 10 µM. If the test compound is a food or food extract, it is included in the diet at about 400 mg/kg-800 mg/kg of food or about 10-30% of the diet. If the compound is administered by injection, it is injected once daily at an amount of about 1 mg/kg to about 100 mg/kg.

Following administration of the test compound, the mice are sacrificed, tissues of interest are removed (such as liver, lung, kidney, colon, mammary gland, or prostate), and cells are grown in culture. The cells are grown under selective conditions to identify cells in which the test compound has inhibited gene silencing, and thereby reactivated expression of the Aprt gene. Cells are plated in medium containing about 10 µg/ml to about 100 µg/ml DAP (which will kill cells which express Aprt), for about 1-3 weeks. The surviving cells are quantified by counting the number of live cells or number or size of colonies of live cells. A statistically significant decrease (such as a decrease of at least 10%, at least 50%, or at least 90%) of the number of surviving or live cells, as compared to the number of live cells from a control sample which has not been treated with the test compound, but has otherwise been treated identically, identifies the compound as an inhibitor of gene silencing.

Test compounds which are identified as inhibitors of gene silencing are further characterized, for example determining the dose that kills 50% of mice ($LD_{50}$) and the maximum tolerated dose.

Example 14

Methods of Identifying Inhibitors of Gene Re-Silencing

This example describes exemplary methods of identification of inhibitors of gene re-silencing using an in vitro assay in cultured cells.

Two cell lines from P19H22 with spontaneously silenced Aprt alleles, D3 and D7, were previously isolated (Cooper et al., *Somat. Cell Mol. Genet.* 17:105-116, 1991). In some examples, these cells are treated with medium containing 10 μg/ml azaserine and 10 μg/ml adenine (AzA medium) to select for spontaneous reactivation of Aprt expression. In other examples, cells are treated with are treated with an inhibitor of DNA methylation (such as about 100 nM to about 10 μM 5-aza-dC), an inhibitor of histone deacetylation (such as about 10 nM to about 1 μM TSA), or a combination thereof to induce reactivation of Aprt expression. Cells which have reactivation of Aprt (as identified by growth in AzA medium) are treated with one or more test compounds which are potential inhibitors of gene re-silencing. The cells are treated with a range of concentrations of the test compounds from about 1 nM to about 1 mM for about one day to about 3 weeks.

The cells are then grown under selective conditions to identify cells in which the test compound has inhibited gene re-silencing, and thereby reactivated expression of the Aprt gene. Cells are plated in medium containing about 10 μg/ml to about 120 μg/ml DAP (which will kill cells which express Aprt), for about 1-3 weeks. The surviving cells are quantified by counting the number of live cells or number or size of colonies of live cells. A statistically significant decrease (such as a decrease of at least 10%, at least 50%, or at least 90%) of the number of surviving or live cells, as compared to the number of live cells from a control sample which has not been treated with the test compound, but has otherwise been treated identically, identifies the compound as an inhibitor of gene re-silencing.

Test compounds which are identified as inhibitors of gene re-silencing are further characterized, for example determining the $LD_{50}$ or $IC_{50}$ of the compound for gene silencing and further testing of the compound in an in vivo model of gene silencing.

Example 15

Evaluation of Compounds Identified as Inhibitors of Gene Silencing

This example describes additional methods that can be used to evaluate compounds identified as potential inhibitors of gene silencing or re-silencing using the methods described above.

Compounds that are identified as potential inhibitors of gene silencing or re-silencing (for example compounds identified using the methods described in Examples 12 through 14) are further evaluated as candidate compounds, for example, for the treatment or prevention of cancer.

The toxicity of the candidate gene silencing (or re-silencing) inhibitor to cells can be initially assessed in vitro using standard techniques. For example, human primary fibroblasts can be treated with a range of concentrations of the selected test compound (such as from 1 nM to 1 mM) and then tested at different time points following treatment for their viability using a standard viability assay. Methods of determining cell survival are well known in the art and include, but are not limited to, the resazurin reduction test (see Fields & Lancaster *Am. Biotechnol. Lab.* 11:48-50, 1993; O'Brien et al., *Eur. J. Biochem.* 267:5421-5426, 2000, and U.S. Pat. No. 5,501,959), the sulforhodamine assay (Rubinstein et al., *J. Natl. Cancer Inst.* 82:113-118, 1990) or the neutral red dye test (Kitano et al., *Euro. J. Clin. Inv.* 21:53-58, 1991; West et al., *J. Investigative Derm.* 99:95-100, 1992) or trypan blue assay. Numerous commercially available kits may also be used, for example the CellTiter 96® AQueous One Solution Cell Proliferation Assay (Promega). Cytotoxicity is determined by comparison of cell survival in the treated culture with cell survival in one or more control cultures, for example, untreated cultures and/or cultures pre-treated with a control compound (typically a known therapeutic), or other appropriate control. Cells can also be assayed for their ability to synthesize DNA, for example, using a thymidine incorporation assay, and for changes in cell cycle dynamics, for example, using a standard cell sorting assay in conjunction with a fluorescence activated cell sorter (FACS).

The general toxicity of the selected compound is tested according to methods known in the art. For example, the overall systemic toxicity of the gene silencing inhibitor is tested by determining the dose that kills 100% of mice (i.e. $LD_{100}$) following a single intravenous injection. The dose that kills 50% of mice (the $LD_{50}$) is determined by administering varying doses of the compound (by any suitable route) and assessing mouse death.

Therapeutic efficacy and toxicity can be determined by standard pharmaceutical procedures such as, for example, by determination of the median effective dose, or $IC_{50}$ (i.e. the dose therapeutically effective in 50% of the population) and the median lethal dose, or $LD_{50}$ (i.e. the dose lethal to 50% of the population). The dose ratio between therapeutic and toxic effects is known as the "therapeutic index," which can be expressed as the ratio, $LD_{50}/IC_{50}$. The data obtained from cell culture assays and animal studies are used to formulate a range of dosage for human or animal use. The dosage contained in such compositions is usually within a range of concentrations that include the $ED_{50}$ and demonstrate little or no toxicity. The dosage varies within this range depending upon the dosage form employed, sensitivity of the subject, and the route of administration and the like.

Efficacy of the inhibitor of gene silencing or re-silencing in treating or preventing cancer can be evaluated in standard models of tumor development and progression. In one example, the efficacy of the identified compound to inhibit tumor growth or decrease tumor size is evaluated in a tumor xenograft model. Mice having one or more human cancer xenografts (such as a breast cancer, lung cancer, colon cancer, or prostate cancer xenograft) are generated using standard methods. Briefly, the xenograft is established in immunodeficient mice (such as SCID or Balb/c nu/nu mice). The xenograft is allowed to grow for a period of time prior to administration of the identified compound (such as 5 days). Alternatively, the identified gene silencing inhibitor can be administered at the same time as the cancer cells, and growth of the xenograft monitored in the absence of further administration of the compound (to determine if xenograft growth can be prevented). The development of the cancer xenograft can be compared to control mice which are not administered the gene silencing inhibitor compound. The amount of compound administered can be 0.1-10 times the $LD_{100}$ dose determined as described above. Following injection (such as 48 hours later), tumors are harvested, fixed and stained with hematoxylin and eosin, and for Ki-67 (proliferative index) and TUNEL (apoptotic index). The percent of tumor within sample is determined by calculating the ratio of viable tumor to total tumor area following image analysis of thin tumor sections. Administration of the compound should reduce tumor volume (such as a reduction of at least 10%, at least 25%, at least 50%, or at least 90%) as compared to control mice (e.g., mice not receiving the compound).

In another example, mice are generated having an experimentally induced cancer, such as treatment with compounds that are known to silence tumor suppressor genes or induce cancers (for example, benzo[a]pyrene, metals (such as iron, nickel, or cobalt), cigarette smoke, the tobacco carcinogens 4-(methylnitrosamino)-1-(3-pyridyl)-1-butanone (NNK) and vinyl carbamate, and the occupational carcinogen methylene chloride). The experimentally-induced tumor is allowed to grow for a period of time prior to administration of the identified compound (such as 5 days). Alternatively, the identified gene silencing or re-silencing inhibitor can be administered at the same time as the conditions that induce the tumor, and growth of the tumor monitored in the absence of further administration of the compound (to determine if xenograft growth can be prevented). The development of the tumor can be compared to control mice which are not administered the gene silencing inhibitor compound. The amount of compound administered can be 0.1-10 times the $LD_{100}$ dose determined as described above. Following injection (such as 48 hours later), tumors are harvested, fixed and stained with hematoxylin and eosin, and for Ki-67 (proliferative index) and TUNEL (apoptotic index). The percent of tumor within sample is determined by calculating the ratio of viable tumor to total tumor area following image analysis of thin tumor sections. Administration of the compound should reduce tumor volume (such as a reduction of at least 10%, at least 25%, at least 50%, or at least 90%) as compared to control mice (e.g., mice not receiving the compound).

Example 16

Kits

Kits are provided which contain the necessary reagents for identifying inhibitors of gene silencing or re-silencing, such as cell lines expressing a repressible promoter operably linked to a selectable marker gene. Such kits can be used with the methods described herein to determine whether a test compound is an inhibitor of gene silencing or re-silencing.

The provided kits may also include written instructions. The instructions can provide calibration curves or charts to compare with the determined (e.g., experimentally measured) values. Kits are also provided to determine elevated or depressed expression of selectable marker mRNA (for example, containing probes or primers) or protein (for example, containing compounds that may be used for selection of cells expressing the selectable marker protein). Additional components may include cell culture medium for growth of the cells and/or additives that can be used to repress expression of the selectable marker gene.

Cell lines, including those disclosed herein, can be supplied in the form of a kit for use in identifying inhibitors of gene silencing. In such a kit, an appropriate amount of one or more cell lines is provided in one or more containers. The cells may be provided frozen in suitable freezing media, for instance. The container(s) in which the cell(s) are supplied can be any conventional container that is capable of holding the supplied form, for instance, microfuge tubes, ampoules, or bottles.

In some examples, the kits can also include probes or primers that can be used to identify increased or decreased amounts of mRNA of the selectable marker. Probes and primers can be included which are useful for quantitative RT-PCR. Methods for developing probes and primers are well known to those of skill in the art (see, e.g., Current Protocols in Molecular Biology, Ausubel, John Wiley & Sons, 1994; Molecular Cloning, A Laboratory Manual, Sambrook et al., Cold Spring Harbor Laboratory, 2001).

In additional examples, the kits can also include compounds that can be used for growth of the cell lines under selective conditions. The compounds may be provided suspended in an aqueous solution or as a freeze-dried or lyophilized powder, for instance. In some examples, the kits include 6-thioguanine, which can be used to selectively kill cells which express HPRT. In other examples, the kits include 2,6-diaminopurine (DAP), which can be used to selectively kill cells which express APRT.

In some examples, the disclosed kits may also include cell culture medium for use in growing the cells. The medium can be provided in any suitable form, such as liquid or as a freeze-dried or lyophilized powder. In other examples, the kits may optionally include compounds that are added to the cell culture medium to repress expression of the selectable marker gene. In some examples, the compound is doxycycline, which can be used to repress expression from a tet-repressible promoter. In other examples, the compound contains a metal ion (for example, iron sulfate, nickel chloride, or cobalt chloride).

In additional embodiments, kits may include the transgenic mice described herein, such as those generated as described in Example 9. In some examples, the transgenic mice include cells containing a repressible promoter operably linked to a repressible promoter (such as a tet-repressible promoter, a BRCA1 promoter, a MLH1 promoter, or an androgen receptor promoter).

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

I claim:

1. A method of identifying an inhibitor of epigenetic gene silencing, comprising:
   inhibiting expression of a selectable marker gene in isolated mammalian cells, wherein the cells comprise a marker gene operably linked to an epigenetically repressed repressible promoter, wherein said repressible promoter is repressed through an external environmental inhibitor that acts upon said repressible promoter to decrease transcriptional activity of said repressible promoter such that transcription of the selectable marker gene is inhibited;
   contacting the cells comprising the epigenetically silenced promoter operably linked to the selectable marker with at least one test compound;
   growing said cells under selective conditions that kill cells expressing the selectable marker or inhibit growth of cells expressing the selectable marker; and
   quantifying the cells treated with the test compound that survive the selective conditions, wherein a decrease in the number of cells that survive the selective conditions as compared to the number of cells from a negative control sample that survive the selective conditions identifies the test compound as an inhibitor of epigenetic gene silencing of the repressible promoter.

2. The method of claim 1, wherein the cells further express a transcription activator protein gene comprising a constitutively active promoter operably linked to a transcription activator protein coding sequence, wherein the transcription activator protein activates expression of the selectable marker gene.

3. The method of claim 1, wherein the repressible promoter comprises an exogenous repressible promoter or a mammalian repressible promoter.

4. The method of claim 3, wherein the exogenous repressible promoter comprises a minimal promoter element and at least one tetracycline responsive element and wherein the external environmental inhibitor comprises tetracycline or a tetracycline analog.

5. The method of claim 4, wherein the cells further express a tetracycline responsive transcription activator protein from a constitutively active promoter.

6. The method of claim 5, wherein the tetracycline responsive transcription activator protein comprises a tetracycline responsive factor fused to an activation domain of a herpes simplex virus transcriptional activator VP-16.

7. The method of claim 3, wherein repressing the external environmental inhibitor comprises hypoxic conditions or metal ions.

8. The method of claim 1, wherein the selectable marker gene comprises hypoxanthine-guanine phosphoribosyltransferase (HPRT), adenine phosphoribosyltransferase (APRT), thymidine kinase, or xanthine-guanine phosphoribosyltransferase (GPT).

9. The method of claim 4, wherein the tetracycline analog comprises doxycycline.

10. The method of claim 1, wherein the repressible promoter comprises a mammalian repressible promoter.

11. The method of claim 10, wherein the mammalian repressible promoter is selected from the group consisting of a BRCA1, MLH1, E-cadherin, estrogen receptor α, androgen receptor, Mcp1, Zac1, Gas1, and Serpin promoter.

12. The method of claim 1, wherein the test compound comprises a small organic molecule, antibody, antisense molecule, or RNAi molecule.

13. The method of claim 1, wherein the test compound comprises an inhibitor of histone deacetylase.

14. The method of claim 13, wherein the inhibitor of histone deacetylase comprises trichostatin A or sulforaphane.

15. The method of claim 1, wherein the test compound comprises a DNA methylation inhibitor.

16. The method of claim 15, wherein the DNA methylation inhibitor comprises 5-aza-2'-deoxycytidine.

17. The method of claim 1 wherein contacting the cells with the test compound occurs within 36 hours of inducing the epigenetic silencing.

18. The method of claim 7, wherein the repressible promoter is a BRCA1 promoter and wherein the external environmental inhibitor comprises hypoxia.

19. The method of claim 1, further comprising removing the environmental inhibitor that decreases transcription of the selectable marker gene prior to contacting the cells with the at least one test compound.

* * * * *